United States Patent
Tian et al.

(10) Patent No.: US 10,183,082 B2
(45) Date of Patent: Jan. 22, 2019

(54) PET PROBES OF RADIOFLUORINATED CARBOXIMIDAMIDES FOR IDO-TARGETED IMAGING

(71) Applicant: H. LEE MOFFITT CANCER CENTER AND RESEARCH INSTITUTE, INC., Tampa, FL (US)

(72) Inventors: Haibin Tian, Tampa, FL (US); Robert J. Gillies, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 15/505,214

(22) PCT Filed: Sep. 9, 2015

(86) PCT No.: PCT/US2015/049152
§ 371 (c)(1),
(2) Date: Feb. 20, 2017

(87) PCT Pub. No.: WO2016/040458
PCT Pub. Date: Mar. 17, 2016

(65) Prior Publication Data
US 2017/0340758 A1 Nov. 30, 2017

Related U.S. Application Data

(60) Provisional application No. 62/047,862, filed on Sep. 9, 2014.

(51) Int. Cl.
| | |
|---|---|
| *A61K 51/00* | (2006.01) |
| *A61M 36/14* | (2006.01) |
| *A61K 51/04* | (2006.01) |
| *C07D 271/08* | (2006.01) |
| *C07D 273/02* | (2006.01) |
| *A61K 49/00* | (2006.01) |

(52) U.S. Cl.
CPC ........ *A61K 51/0453* (2013.01); *C07D 271/08* (2013.01); *C07D 273/02* (2013.01); *A61K 49/00* (2013.01)

(58) Field of Classification Search
CPC .. A61K 51/0453; A61K 49/00; C07D 271/08; C07D 273/02
USPC ........................................................ 424/1.89
See application file for complete search history.

(56) References Cited

FOREIGN PATENT DOCUMENTS

WO    WO-2006122150 A1 * 11/2006 ........... C07D 271/08

OTHER PUBLICATIONS

Lappchen et al. Appl. Rad. Isot. 70 (2012) 205-209.*
Batista et al. Mol. Imaging Biol. (2009) 11: 460-366.*
Zhang et al. Curr. Top. Med. Chem. 2007, 7, 1817-1828.*
Dolušić, E. et al. "Indoleamine 2,3-dioxygenase inhibitors: a patent review (2008-2012)" *Expert Opinion on Therapeutic Patents*, Oct. 2013, 23(10):1367-1381, abstract.
Friberg, M. et al. "Indoleamine 2,3-Dioxygenase Contributes to Tumor Cell Evasion of T Cell-Mediated Rejection" *International Journal of Cancer*, 2002, 101:151-155.
Huang, C. et al. "Radiosynthesis and Biological Evaluation of alpha-[F-18]Fluoromethyl Phenylalanine for Brain Tumor Imaging" *Nuclear Medicine and Biology*, May 2013, 40(4):498-506.
Huang, X. et al. "Synthesis of [$^{18}$F] 4-amino-N-(3-chloro-4-fluorophenyl)-N'-hydroxy-1,2,5-oxidazole-3-carboximidamide (IDO5L): a novel potential PET probe for imaging of IDO1 expression" *Journal of Labelled Compounds and Radiopharmaceuticals*, Feb. 18, 2015, 58:156-162.
Juhász, C. et al. "Quantification of Tryptophan Transport and Metabolism in Lung Tumors Using PET" *The Journal of Nuclear Medicine*, Mar. 2009, 50(3):356-363.
Koblish, H.K. et al. "Hydroxyamidine Inhibitors of Indoleamine-2,3-dioxygenase Potently Suppress Systemic Tryptophan Catabolism and the Growth of IDO-Expressing Tumors" *Molecular Cancer Therapeutics*, Feb. 2, 2010, 9(2):489-498.
Lazarova, N. et al. "Integration of a microwave reactor with Synthia to provide a fully automated radiofluorination module" *Journal of Labelled Compounds and Radiopharmaceuticals*, 2007, 50:463-465.
Lindström, V. et al. "Indoleamine 2,3-Dioxygenase Activity and Expression in Patients With Chronic Lymphocytic Leukemia" *Clinical Lymphoma, Myeloma & Leukemia*, Oct. 2012, 363-365.
Liu, X. et al. "Indoleamine 2,3-Dioxygenase, an Emerging Target for Anti-Cancer Therapy" *Curr. Cancer Drug Targets*, 2009, 9(8):938-952, abstract.
Liu, X. et al. "Selective inhibition of IDO1 effectively regulates mediators of antitumor immunity" *Blood*, Apr. 29, 2010, 115(17):3520-3530.
Liu, X.-Q. et al. "Up-regulated expression of indoleamine 2,3-dioxygenase 1 in non-Hodgkin lymphoma correlates with increased regulatory T-cell infiltration" *Leukemia & Lymphoma*, Feb. 2014, 55(2):405-414.
Malachowski, W.P. et al., "A new cancer immunosuppression target: Indoleamine 2,3-dioxygenase (IDO). A review of the IDO mechanism, inhibition and therapeutic applications", *Drugs of the Future*, 2005, 30(9):897, abstract.
Muller, A.J. et al. "Inhibition of indoleamine 2,3-dioxygenase, an immunoregulatory target of the cancer suppression gene Bin1, potentiates cancer chemotherapy" *Nature Medicine*, Mar. 2005, 11(3):312-319.
Munn, D.H. et al. "Inhibition of T Cell Proliferation by Macrophage Tryptophan Catabolism" *The Journal of Experimental Medicine*, May 3, 1999, 189(9):1363-1372.

(Continued)

*Primary Examiner* — Michael G. Hartley
*Assistant Examiner* — Sean R Donohue
(74) *Attorney, Agent, or Firm* — Saliwanchik, Lloyd & Eisenschenk

(57) ABSTRACT

$^{18}$F labeled IDO1 imaging constructs are constructed for positron emission tomography (PET). Synthetic methodology involves the coupling of a 1-fluoro-2-halo-4-aminobenzene and a 4-mino-N-hydroxy-1,2,5-oxadiazole-3-carboximidoyl chloride wherein at least one of the coupled compounds comprises an $^{18}$F. The $^{18}$F labeled IDO1 imaging constructs are useful for imaging cancer cells in a patient.

9 Claims, 16 Drawing Sheets

(56) References Cited

OTHER PUBLICATIONS

Pilotte, L. et al. "Reversal of tumoral immune resistance by inhibition of tryptophan 2,3-dioxygenase" *Proceedings of the National Academy of Sciences of the United States*, Feb. 14, 2012, 109(7):2497-2502.

Platten, M. et al. "Cancer immunotherapy by targeting IDO1/TDO and their downstream effectors" *Frontiers in Immunology*, Jan. 12, 2015, 5(673):1-7.

Seimbille, Y. et al. "Fluorine-18 labeling of 6,7-disubstituted anilinoquinazoline derivatives for positron emission tomography (PET) imaging of tyrosine kinase receptors: synthesis of $^{18}$F-Iressa and related molecular probes" *Journal of Labelled Compounds and Radiopharmaceuticals*, 2005, 48:829-843.

Sugae, S. et al. "Fluorine-18-labeled 5-fluorouracil is a useful radiotracer for differentiation of malignant tumors from inflammatory lesions" *Annals of Nuclear Medicine*, 2008, 22:65-72.

Takikawa, O. et al. "Mechanism of Interferon-γ Action—Characterization of Indoleamine 2,3-Dioxygenase in Cultured Human Cells Induced by Interferon-γ and Evaluation of the Enzyme-Mediated Tryptophan Degradation in its Anticellular Activity" *The Journal of Biological Chemistry*, Feb. 5, 1988, 263(4):2041-2048.

Uyttenhove, C. et al. "Evidence for a tumoral immune resistance mechanism based on tryptophan degradation by indoleamine 2,3-dioxygenase" *Nature Medicine*, Oct. 2003, 9(10):1269-1274.

Vacchelli, E. et al. "Trial watch: IDO inhibitors in cancer therapy" *OncoImmunology*, Nov. 1, 2014, 3(10):e957994-1-e957994-10.

Vanbrocklin. H.F. et al. "Synthesis of [18]Fluoroanilines: Precursors to [18F]Fluoroanilinoquinazolines" *Journal of Labelled Compounds and Radiopharmaceuticals*, 2001, 44(1):S880-S882.

Yoshikawa, T. et al. "Serum concentration of L-kynurenine predicts the clinical outcome of patients with diffuse large B-cell lymphoma treated with R-CHOP" *European Journal of Haematology*, 2009, 84:304-309.

Yue, E.W. et al. "Discovery of Potent Competitive Inhibitors of Indoleamine 2,3-Dioxygenase with in Vivo Pharmacodynamic Activity and Efficacy in a Mouse Melanoma Model" *Journal of Medicinal Chemistry*, Jun. 9, 2009, 52(23):7364-7367.

Zitron, I.M. et al. "In vivo metabolism of tryptophan in meningiomas is mediated by indoleamine 2,3-dioxygenase 1" *Cancer Biology & Therapy*, Apr. 2013, 14(4):333-339.

Clinical Trials [online], retrieved from the internet, URL: clinicaltrials.gov/ct2/resutls?term=NCT01604889, "A Phase 1/2 Randomized, Blinded, Placebo Controlled Study of Ipilimumab in Combination With INCB024360 or Placebo in Subjects With Unresectable or Metastatic Melanoma".

Clinical Trials [online], retrieved from the internet, URL: clinicaltrials.gov/ct2/results?term=NCT01961115, "Epacadostat and Vaccine Therapy in Treating Patients With Stage III-IV Melanoma".

Clinical Trials [online], retrieved from the internet, URL: clinicaltrials.gov/ct2/results?term=NCT01042535, "Vaccine Therapy and 1-MT in Treating Patients With Metastatic Breast Cancer".

* cited by examiner

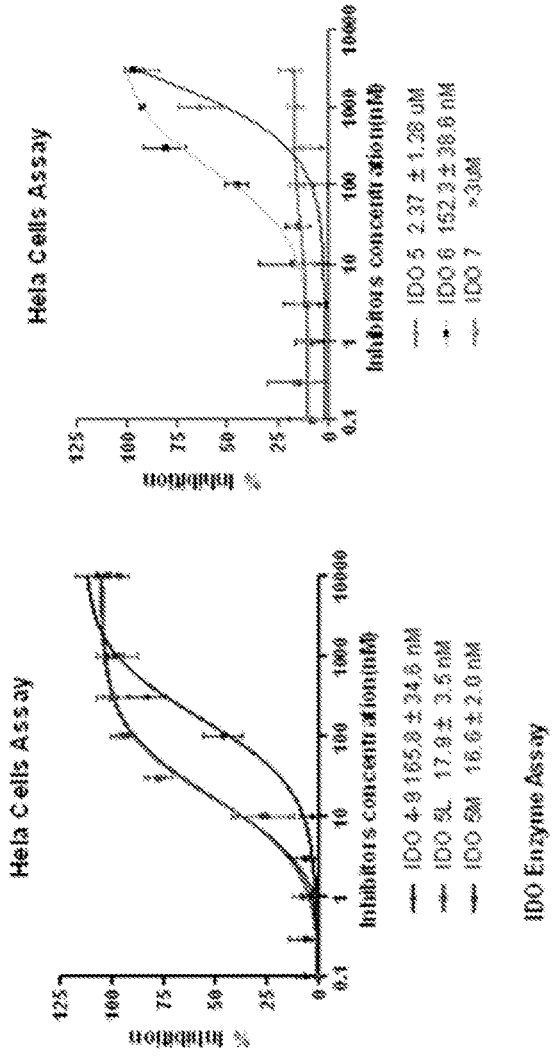
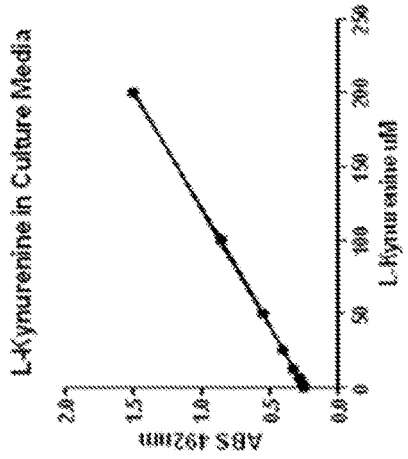
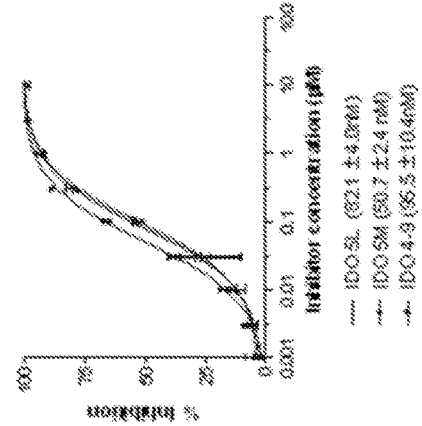
FIG. 7A
FIG. 7B
FIG. 7C
FIG. 7D

PET PROBES OF RADIOFLUORINATED CARBOXIMIDAMIDES FOR IDO-TARGETED IMAGING

CROSS-REFERENCE TO RELATED APPLICATION

The present application is the national Stage of international Application Number PCT/US2015/049152, filed Sep. 9, 2015, which claims the benefit of U.S. Provisional Application Ser. No. 62/047,862, filed Sep. 9, 2014, each of which is hereby incorporated by reference herein in its entirety, including any figures, tables, nucleic acid sequences, amino acid sequences, or drawings.

BACKGROUND OF THE INVENTION

Indoleamine 2,3-dioxygenase-1 (IDO1) catabolizes the L-tryptophan (Trp) to yield L-N-formylkynurenine (Kyn), which is the initial and rate-limiting step in Trp degradation pathway. IDO1 is expressed in a variety of tissues and particularly high level expression observed in placenta of pregnant females, various human tumor cells, and dendritic cells that localize to the tumor-draining lymph nodes [1-3]. Increasing in vivo and in vitro pieces of evidence implicated that IDO1 is involved in immune escape of tumor cells, and blockage of its activity can directly increase the ability of tumor-bearing mice to reject tumors [2,4-7]. Recent studies demonstrated that the expression level of IDO increased in various tumors such as in lungs, prostate, and pancreas, lymphoma, and breast cancers. It is reported that patients with high level of IDO1 expression were correlated with later clinical phases and larger tumors and indicated a worse prognosis in various cancers such as diffuse large B-cell lymphoma and chronic lymphocytic leukemia [8-10]. Currently, two IDO1 inhibitors 1-methyl-D-tryptophan and INCB024360 are used in phase II clinical trials for the treatment of breast cancer and melanoma, respectively [11].

Molecular imaging methods such as positron emission tomography (PET) have the potential to generate IDO1 expression profile in vivo and provide valuable information on how the IDO pathway responds to the immune-modulating therapies. α-[$^{11}$C] methyl-L-tryptophan (α-$^{11}$C-AMT), an IDO1 substrate, has been reported to be associated with the IDO1 expression levels in the brain and lung tumors [12,13]. However, IDO1 only was involved in the first step of the kynurenine pathway, while increased α-$^{11}$C-AMT uptake by cells is a complicated issue because of many other enzymes involved in tryptophan transportation and metabolism pathway. Therefore, there is an urgent need to develop a specific PET imaging agent targeted to IDO1 for cancer imaging.

BRIEF SUMMARY OF THE INVENTION

Embodiments of the invention are directed to $^{18}$F labeled IDO1 imaging constructs of the structure:

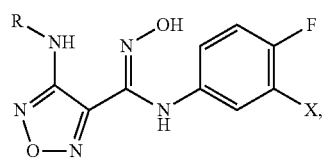

where the fluorine is optionally $^{18}$F, X is a halogen and R is H, $C_1$-$C_8$ alkyl, $C_1$-$C_8$ alkylcarbonyl, phenyl, phenylcarbonyl, wherein R is optionally substituted with one or more $C_1$-$C_8$ alkyl, phenyl, phenylHC=N—O—, where the substituent is optionally substituted with a fluorine, where the fluorine is optionally $^{18}$F, and wherein at least one fluorine is $^{18}$F. An embodiment of the invention is directed to a method of preparing the $^{18}$F labeled IDO1 imaging construct where a 4-amino-N-hydroxy-1,2,5-oxadiazole-3-carboximidoyl chloride of the structure:

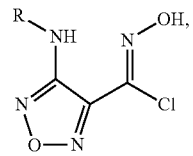

where R is H, $C_1$-$C_8$ alkyl, $C_1$-$C_8$ alkylcarbonyl, phenyl, phenylcarbonyl, wherein R is optionally substituted with one or more $C_1$-$C_8$ alkyl, phenyl, phenylHC=N—O—, where the substituent is optionally substituted with a fluorine is combined with a 1-$^{18}$F-2-halo-4-aminobenzene with the 4-amino-N-hydroxy-1,2,5-oxadiazole-3-carboximidoyl chloride wherein one or both of the molecules contain an $^{18}$F.

An embodiment of the invention is directed to a method of performing positron emission tomography (PET), comprising injecting a solution comprising an $^{18}$F labeled IDO1 imaging construct into a patient suspected of having cancer, such as breast cancer.

BRIEF DESCRIPTION OF THE DRAWINGS

FIGS. 7A-7D. Inhibition of IDO activity. FIGS. 7 and 7B: IFN-γ induces IDO activity in the Hela cell lines, the activity of which is inhibited by 6 different IDO inhibitors (FIG. 7A: IDO4-9, IDO5l, IDO5m; and FIG. 7B: IDO5, IDO6, IDO7). FIG. 7C: results of IDO1 enzyme inhibition assay. FIG. 7D: the standard curve of L-Kynurenine's UV absorbance under various concentrations. The IDO enzyme assay (enzolifesciences.com; ALX-201-333-C050) was performed at room temperature as described in the literature with minor revision. (J. Bio. Chem. 263, 4, 2041-2048, 1988). Briefly, in each well of a 96 well-plate, 10 μL of Human IDO (0.05 mg/mL in KHPO4, 50 mM, PH 6.5) was added into 40 μL buffer (KHPO4, 50 mM, PH 6.5, DMSO 2.5% v/v) containing different concentrations of inhibitors (2000, 600, 200, 60, 20, 6, 2, 0.6, 0.2 μM). Next, 50 μL of the substrate buffer (4 mM L-tryptophan (#T0254, Sigma), 40 mM ascorbate, 20 uM methylene blue (#M44907, Sigma), 0.2 mg/mL catalase (#C30, Sigma)) was mixed into each well and incubated at 37° C. for 2 hours. Next, 10 μL of 6.1N trichloroacetic acid (#T0699, Sigma) was mixed into each well and incubated at 52° C. for 30 min to hydrolyze N-formylkynurenine produced by IDO to kynurenine. The reaction mixture was incubated with 100 μL of 0.02 g/mL p-(Dimethylamino) benzaldehyde (#mk1836100, Fisher) in acetic acid at room temperature for 10 minutes. The yellow color derived from kynurenine was measured at 492 nm using microplate reader. L-Kynurenine (#K8625, Sigma), which was used as the standard, was prepared in a series of concentrations (1000, 500, 200, 100, 50, 20, 10 μM). The percent inhibition at individual concentrations was determined, and the average values of duplicates were obtained. The data was processed using nonlinear regression to generate IC50 values (Prism Graphpad).

FIG. 10A: Cell uptake of 18F-IDO at 30 minutes, 60 minutes, and 120 minutes. FIG. 10B: Cell uptake of 18F-IDO by Hela cells at 120 minutes with the inhibitor of IDO, 1-L-MT.

FIG. 12A: $^{18}$F-IDO5L microPET/CT scans of CLL tumor mice. Mice were imaged 1 hour after i.p. injection of the probe. FIG. 12B: $^{18}$F-IDO5L microPET/CT scans of wild-type mice as control. FIG. 12C: $^{18}$F-DG microPET/CT scans of the same mice, imaged 1 day after the $^{18}$F-IDO5L microPET/CT scans. $^{18}$F-IDO5L microPET/CT can predict IDO expression-related immune responses in CLL mouse model.

FIG. 13: $^{18}$F-IDO5L microPET/CT imaging at 10-minute time point. FIG. 14: $^{18}$F-IDO5L microPET/CT imaging at 30-minute time point. FIG. 15: $^{18}$F-IDO5L microPET/CT imaging at 60-minute time point.

DETAILED DESCRIPTION OF THE INVENTION

Among the potent inhibitors reported in the literature, the most potent inhibitor of IDO1 is INCB024360 ($IC_{50}$=7.1 nM, HeLa cell assay) [6]. The carboximidamide compound IDO5L is one of the highest potent inhibitors of the IDO1 ($IC_{50}$=19 nM, HeLa cell assay) [14]. Moreover, the reported rapid clearance rate (t½<0.5 h, via oral administration) of IDO5L indicated the faster clearance rate after i.v. administration during PET imaging. This fast clearance may be preferred for $^{18}$F-PET imaging agent for less imaging background.

Recent studies indicate that tryptophan oxidation via the enzyme IDO can modulate immunoresistance of cancers. In vivo detection of IDO may facilitate therapeutic measures by identifying patients likely to benefit and to quantitatively monitor IDO inhibition in vivo by effectively evaluating the number of receptors. The present invention concerns novel $^{18}$F-carboximidamide constructs and their use as positron emission tomography (PET) imaging agent. The inventors utilized $^{18}$F-labeled aniline as intermediate in [$^{18}$F]-radiolabeling chemistry for the radiosynthesis of $^{18}$F-IDO5L as a novel IDO1-targeted tracer. $^{18}$F-IDO5L is a highly potent inhibitor of IDO1 with low nanomolar $IC_{50}$ and was synthesized by a three-step radiolabeling procedure. The tracer was obtained in 12-20% overall decay-corrected radiochemical yield from aqueous [$^{18}$F]fluoride. Under the optimized labeling conditions, chemically and radiochemically pure (>98%) $^{18}$F-IDO5L was obtained with specific radioactivity ranging from 11 to 15 GBq/μmol at the end of synthesis within ~90 min, and the decay-corrected radiochemical yield was 18.2±2.1% (n=4).

The fluorine-18-labeled carboximidamide compound IDO5L and other constructs of the invention can serve as novel probes for the PET imaging to generate an IDO1 activity profile in vivo that is useful to predict IDO1-related cancer diagnostic and monitor therapeutic efficacy of IDO1 inhibitors. For the first time, the inventors synthesized $^{18}$F-carboximidamide compound IDO5L as a novel potential PET agent by utilizing [$^{18}$F]3-chloro-4-fluoroaniline as intermediate. Huang X. et al. ("Synthesis of [18F] 4-amino-N-(3-chloro-4-fluorophenyl)-N'-hydroxy-1,2,5-oxadiazole- 3-carboximidamide (IDO5L): a novel potential PET probe for imaging of IDO1 expression", *J. Label Compd. Radiopharm*, 2015, 58:156-162) is incorporated herein by reference in its entirety.

Figure 1:
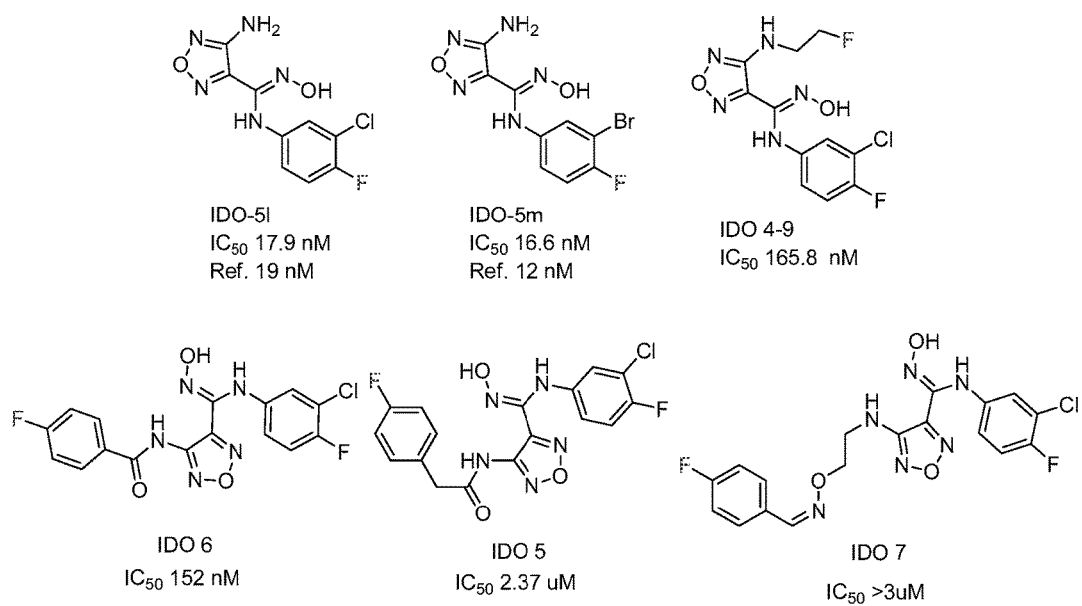
FIG. 1 shows the structure of exemplary IDO1 inhibitors according to embodiments of the invention, where one or more of the Fs are $^{18}$F, and their $IC_{50}$.

Embodiments of the invention are to $^{18}$F labeled IDO1 imaging constructs, their method of preparation, and their use for clinically relevant imaging modalities for the diagnosis and monitoring of breast and other cancers by PET radiochemistry that is readily available to many hospitals with cyclotrons and PET scanners. $^{18}$F-IDO1 inhibitors with appropriate IC50s can be determined by hela cells assays where the level for cytotoxicity ($IC_{50}$) is significantly greater than the PET-Imaging dose (about 0.1 nM) and are useful as imaging agents. Exemplary IDO1 inhibitors and their $IC_{50}$ values are shown in FIG. 1. Cytotoxicity values for IDO inhibitors IDO5l, IOD5m, IDO4-9 and IDO6 on 4 different cell lines (Hela, MDA-MB-231, MCF-7 and HuMEC) evaluated with a cell proliferation assay using ALAMAR-BLUE™ cell viability reagent indicated that the IDO inhibitors display no cytotoxicity to the four tested cell lines at concentration of 100 nM, which is 1000 times of PET-Imaging dose (0.1 nM) and even the more cytotoxic compounds display $IC_{50}$ values that are about 100 times greater than the imaging dosage.

The solution of the imaging agent can be an aqueous solution that can include various other components including other physiologically active or inactive components, such as drugs, preservatives, surfactants, salts, or any other components to facilitate administration or imaging analysis.

A number of medical diagnostic procedures, including PET, and Single Photon Emission Computed Tomography (SPECT) utilize radiolabeled compounds. PET and SPECT are very sensitive techniques and require small quantities of radiolabeled compounds, called tracers. The labeled compounds are transported, accumulated and may be processed in vivo in the same way as the corresponding non-radioactively labeled compounds. Tracers, or probes, can be radiolabeled with a radionuclide useful for PET imaging, such as $^{18}$F.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function.

The accurate detection of diseased tissue requires both spatial and biochemical feedback. For example, a two-step diagnosis involving both CT-based analysis and tissue biopsy guides clinicians in helping elucidate the presence and nature of a suspected disease. These two steps are necessary because CT analysis, devoid of any biochemical information, has limited benefit without complimentary information. In contrast, other imaging modalities can provide both spatial and biochemical information instantaneously. In vivo imaging of biochemical reporters provides critical biochemical information, deriving from the up- or down-regulation of specific cellular reporters, and in tandem, providing key spatial information. For instance, PET imaging, routinely used by clinicians, can be used to accurately detect tumors and monitor tumor progression as a function of time.

Among the biomarkers of cancer, IDO1 is an excellent target because it is overexpressed in localized cancer cells and tumor-draining lymph nodes to help tumor cells evade immune surveillance. Conventional methods such as analysis of serum concentration of L-kynurenine and immunocytochemical staining of biopsy samples fail to generate a localized IDO1 expression profile in the whole body. The imaging agents of the invention exhibit affinity toward IDO1, can be used as a tracer for PET imaging. The PET images provide an IDO1 expression profile to facilitate more precise tumor staging and prognostic evaluations, and can be used to monitor the response of a cancer to therapy.

An aspect of the invention includes a method of PET, comprising injecting a solution comprising an $^{18}$F labeled IDO1 imaging construct into a patient suspected of having cancer. The method involves detecting the presence of retained radioactivity in the patient. The detecting step employs PET for monitoring a distribution of the imaging construct within the body or within a portion thereof for visualization. A PET scanner produces three-dimensional images of the tracer concentration within the body or body portion through computer analysis.

The imaging construct can be administered to the patient once or multiple times, and imaged multiple times over time to monitor IDO1 expression as a function of time (e.g., over days, weeks, or months). The solution comprising the $^{18}$F labeled IDO1 imaging construct may be administered to the patient systemically or locally (e.g., at a tissue or anatomical site of suspected cancer).

Another aspect of the invention includes a method for imaging an imaging construct in vivo, the method comprising contacting the imaging construct of the invention to a cell and imaging the construct in vivo. The method involves detecting the presence of retained radioactivity in the cell in vivo for visualization.

The methods of the invention can employ additional imaging techniques in conjunction with PET, such as X-ray computed tomography (CT), magnetic resonance imaging (MRI), functional MRI (fMRI), ultrasound, and single-photon emission computed tomography (SPECT).

Another aspect of the invention includes a method for treating cancer in a patient, comprising administering a treatment for the cancer to the patient; and injecting a solution comprising an $^{18}$F labeled IDO1 imaging construct of the invention into the patient for PET imaging. In some embodiments, the treatment is administered before injecting the solution. In some embodiments, the treatment is administered after injecting the solution. In some embodiments, the solution is injected before administering the treatment to the patient, and the solution is administered after administering the treatment to the patient. For example, a baseline IDO1 profile may be established by injecting the solution and conducting PET imaging on the patient; administering the treatment to the patient; and, after a period of time (e.g., minutes, hours, days, months), injecting the solution and conducting PET imaging on the patient again to determine whether IDO1 signal (imaging data corresponding to, e.g., IDO1 expression) has been reduced, increased, or stayed the same following the treatment. The IDO1 imaging data obtained after treatment can be compared to reference IDO1 imaging data. Reference IDO1 imaging data may be IDO1 imaging data obtained from that patient from a prior time point (e.g., before or after administration of a cancer treatment), or IDO1 imaging data reflecting IDO1 in a population of normal (non-cancer) patients or reflecting IDO1 in a population of cancer patients such as that is clinical responding to treatment or cancer is not clinically responding to treatment.

In some embodiments, the solution comprising the imaging construct is administered and the patient is PET imaged about 30 minutes after administration of the cancer treatment. In some embodiments, the solution comprising the imaging construct is injected and the patient is PET imaged 1 to 3 months after administration of the cancer treatment and, optionally, the solution is injected and patient imaged one or more times thereafter to monitor the patient over time.

Injection of the solution comprising the imaging construct can be carried out multiple times over time to monitor treatment of the cancer with, with the same treatment or with different treatments (as the treatment strategy for a patient may change). Optionally, if IDO1 signal has increased or stayed the same following treatment, a different treatment strategy can be employed in which a different or additional treatment is selected and administered to the patient (e.g., an additional or different anti-cancer agent).

In some embodiments, the cancer is one in which indoleamine 2,3-dioxygenase-1 (IDO1) is over-expressed relative to normal tissue.

In some embodiments, the treatment for the cancer comprises administration of surgery, radiation, chemotherapy, immunotherapy, or a combination of two or more of the foregoing. In some embodiments, the treatment comprises administering at least one inhibitor of indoleamine 2,3-dioxygenase-1 (IDO1) to the patient, such as 1-methyl-tryptophan (1-MT), Indoximod (NLG-8189; CAS Number: 110117-83-4), the D isomer of 1-MT; Epacadostat (INCB024360); norharmane (CAS Number: 244-63-3); CAY10581 (CAS Number: 1018340-07-2); NLG919; F001287; hybrid hypoxia-targeting IDO inhibitor (e.g., TX-2274); interfering RNA molecules (e.g., siRNA) specific for IDO; and interfering antibodies or antibody fragments specific for IDO.

In some embodiments, the treatment comprises administering a combination of an inhibitor of IDO1 and a different cancer treatment simultaneously or consecutively. In some embodiments, the different treatment comprises radiation, chemotherapy, immunotherapy, or a combination of two or more of the foregoing.

Imaging agents (constructs) according to embodiments of the various aspects of the invention (compositions of matter and methods) have the structure I:

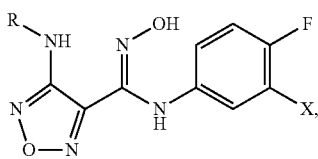

where the fluorine is optionally $^{18}F$, X is a halogen and R is H, $C_1$-$C_8$ alkyl, $C_1$-$C_8$ alkylcarbonyl, phenyl, phenylcarbonyl, wherein R is optionally substituted with one or more $C_1$-$C_8$ alkyl, phenyl, phenylHC=N—O—, where the substituent is optionally substituted with a fluorine, where the fluorine is optionally $^{18}F$, and wherein at least one fluorine is $^{18}F$. For example, IDO4-9 and IDO6 can have the $^{18}F$ other than on the 3-halo-4-fluoro phenyl group, as shown in Scheme 1, below.

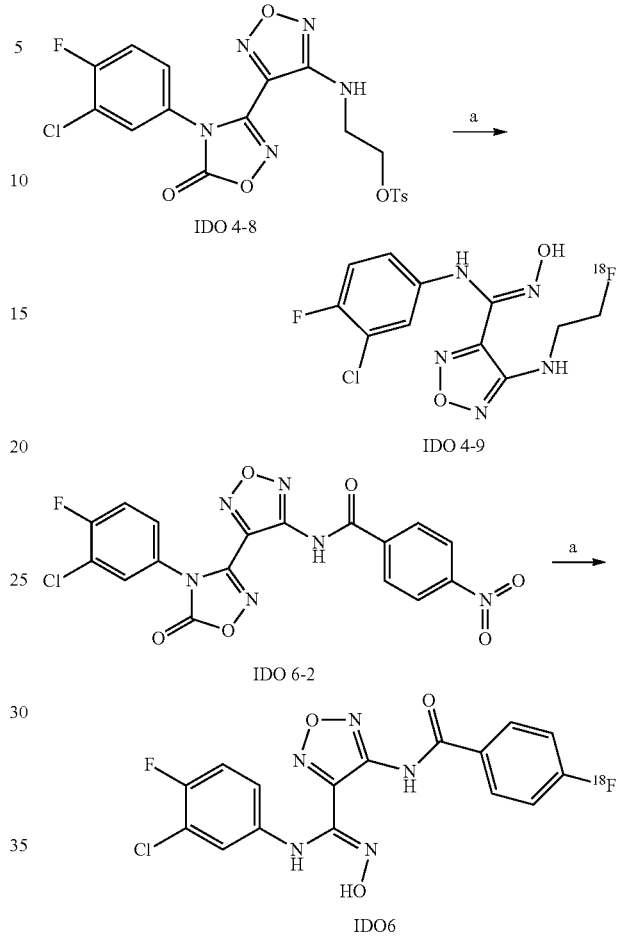

Scheme 1. Synthesis of $^{18}F$ labeled IDO4-9 and IDO6

Reagents: a. 1)K[$^{18}F$]F/$K_2CO_3$, $K_{222}$; 2) 2M NaOH.

In vitro competitive cell binding assays using Murine RMA lymphoma cells as model cell lines, due to reported repeated administrations of INFγ-NGR increase IDO1 activity in the RMA lymphoma tumors, can be used to determine in vitro cell binding, where the RMA cells are treated by INFγ-NGR to increase IDO1 expression. The activity of IDO1 is determined by its ability to convert L-Tryptophan to L-kynurenine following reported method.[15] Subsequent cell treatment using IDO1 inhibitors, either 1-D-MT or IDO 5l, treated or untreated cells can be incubated $^{18}F$ labeled tracer can be used to establish the relationship between retention of tracer and IDO expression for assessment of the quality of the $^{18}F$-IDO1 imaging constructs. The imaging construct can be contacted to the cell once or multiple times, and imaged multiple times over time to monitor IDO1 expression as a function of time (e.g., over days, weeks, or months). The cell may be a cancer cell or normal cell. In some embodiments, the cell is a cancer cell that has arisen in the patient. In some embodiments, the cell is a cancer cell that has been implanted in a non-human animal, e.g., as a xenograft model.

To establish $^{18}F$-IDO1imaging construct stability, metabolite analyses can be carried out where the $^{18}F$-IDO1imaging construct is incubated with mice blood ex vivo for an appropriate time interval (e.g., 45 min), and the blood sample subsequently analyzed by HPLC to detect decomposition of the imaging construct. Subsequently or alternatively, mice can be injected intravenously with an $^{18}$F-IDO1 imaging construct with uptake, for example, of up to 45 minutes before tissue removal and homogenization with whole-blood sampling performed via retro-orbital eye bleeding, followed by centrifugation to obtain plasma and after a multi-step sample treatment, analysis by HPLC.

Pharmacokinetic and biodistribution of normal and RMA lymphoma model mice can be carried out to determine the retention time of the $^{18}$F-IDO1 imaging construct in plasma and other organs, where C57BL/6 wild-type can be used. The mice can be challenged with s.c. injection in the left flank of RMA living cells and then treated with INFγ-NGR injection after 6-10 days with serum concentration ratios of L-kynurenine and L-tryptophan monitored using a state of the art method. Untreated mice and treated mice can be injected with a single dose of an $^{18}$F-IDO1 imaging construct. At various time points after injection, mice can be sacrificed by injection of a lethal dose of anesthesia (20 L of Ketalar-Rompun per gram of body weight: Ketalar [50 mg/mL; Pfizer], 10 mg/mL; Rompun [20 mg/mL; Bayer]), followed by heart puncture and exsanguination with a 1-mL syringe rinsed with heparin (5,000 IE/mL; Leo Pharma). Samples of blood, colon, lung, liver, spleen, pancreas, salivary gland, stomach, kidney, muscle, and bone can be collected and weighed, their radioactivity measured such that the tissue uptake can be calculated as percentage of injected radioactivity per gram.

Ultimately, the effectiveness of a $^{18}$F-IDO1 imaging construct, according to an embodiment of the invention, can be characterized by small-animal PET/CT studies. In vivo studies of PET/CT can be performed on normal mice and RMA tumor model mice using a micro-PET/CT with mice imaged 60 minutes after intravenous injection of $^{18}$F labeled tracers. From the PET imaging data, the $^{18}$F-IDO1 imaging construct uptake and localization (measured by SUV) of tumor model mice can be detected in Regions of Interest (ROI). The tumor model mice can be treated with various doses of IDO inhibitor 1-D-MT. The mice can be imaged prior to and during treatment with the $^{18}$F-IDO1 imaging construct. Effects, such as tumor volume and kyn/Trp level in tumor and plasma can be compared with ROI of PET imaging.

The methods of the invention include methods for the diagnosis and monitoring of cancer, such as breast cancer, lung cancer, prostate cancer, pancreatic cancer, lymphoma, and melanoma. Cancers within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain.

Representative cancer types that can be the diagnosed, monitored, and/or treated in accordance with the methods of the invention include, but are not limited to, those listed in Table 1.

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |
| Burkitt's Lymphoma | Lymphoma, Non-Hodgkin's During Pregnancy |
| Carcinoid Tumor, Childhood | |
| Carcinoid Tumor, Gastrointestinal | Lymphoma, Primary Central Nervous System |

-continued

Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult Primary, Metastatic
Stomach (Gastric) Cancer
Stomach (Gastric) Cancer, Childhood
Supratentorial Primitive Neuroectodermal Tumors, Childhood
T-Cell Lymphoma, Cutaneous, see Mycosis Fungoides and Sézary Syndrome
Testicular Cancer
Thymoma, Childhood
Thymoma and Thymic Carcinoma
Thyroid Cancer
Thyroid Cancer, Childhood
Transitional Cell Cancer of the Renal Pelvis and Ureter
Trophoblastic Tumor, Gestational
Unknown Primary Site, Carcinoma of, Adult
Unknown Primary Site, Cancer of, Childhood
Unusual Cancers of Childhood
Ureter and Renal Pelvis, Transitional Cell Cancer
Urethral Cancer
Uterine Cancer, Endometrial
Uterine Sarcoma
Vaginal Cancer
Visual Pathway and Hypothalamic
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma
Pregnancy and Breast Cancer
Pregnancy and Hodgkin's Lymphoma
Pregnancy and Non-Hodgkin's Lymphoma
Primary Central Nervous System Lymphoma
Prostate Cancer
Rectal Cancer
Renal Cell (Kidney) Cancer
Renal Cell (Kidney) Cancer, Childhood
Renal Pelvis and Ureter, Transitional Cell Cancer
Retinoblastoma
Rhabdomyosarcoma, Childhood
Salivary Gland Cancer
Salivary Gland Cancer, Childhood
Sarcoma, Ewing's Family of Tumors
Sarcoma, Kaposi's
Sarcoma, Soft Tissue, Adult
Sarcoma, Soft Tissue, Childhood
Sarcoma, Uterine
Sezary Syndrome
Skin Cancer (non-Melanoma)
Skin Cancer, Childhood Glioma, Childhood
Vulvar Cancer
Waldenström's Macroglobulinemia
Wilms' Tumor As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), or by needle aspirations. The use of these latter techniques is more common in early detection. Molecular and phenotypic analysis of cancer cells within a tissue will usually confirm if the cancer is endogenous to the tissue or if the lesion is due to metastasis from another site. The term "tumor" is inclusive of solid tumors and non-solid tumors.

The methods of the invention may further include identifying the patient as one having the cancer before, during, and/or after administration (e.g., injection) of an imaging construct and, optionally, imaging of the patient. The cancer may be one that over-expresses IDO1 relative to normal (non-cancerous) tissue.

The methods of the invention may further include treating the patient before, during, and/or after administration (e.g., injection) of an imaging construct. In some embodiments, the treatment comprises surgery, radiation, an anti-cancer agent (such as chemotherapy or immunotherapy), or a combination of two or more of the foregoing. In some embodiments, the method comprises administering a treatment to the patient before, during, and/or after administration (e.g., injection) of an imaging construct and, optionally, imaging of the patient. When an anti-cancer agent is administered simultaneously with the imaging construct, the anti-cancer agent may be administered within the same composition (formulation) or separate compositions.

In some embodiments, the treatment comprises administering one or more inhibitors of IDO1 to the patient. In some embodiments, the IDO1 inhibitor is 1-methyl-tryptophan (1-MT), Indoximod (NLG-8189; CAS Number: 110117-83-4), the D isomer of 1-MT; Epacadostat (INCB024360); norharmane (CAS Number: 244-63-3); CAY10581 (CAS Number: 1018340-07-2); NLG919; F001287; hybrid hypoxia-targeting IDO inhibitor (e.g., TX-2274); interfering RNA molecules (e.g., siRNA) specific for IDO; and interfering antibodies or antibody fragments specific for IDO. Examples of IDO1 inhibitors that may be utilized and cancers are described in Vacchelli E et al., "Trial Watch: IDO Inhibitors in Cancer Therapy", *Oncolmmunology*, Nov. 1, 2014, 3:10, e957994; Malachowski et al., "A new cancer immunosuppression target: Indoleamine 2,3-dioxygenase (IDO). A review of the IDO mechanism, inhibition and therapeutic applications", Drugs Fut., 2005, 30(9):897; Platten et al., "Cancer Immunotherapy by Targeting IDO1/TDO and Their Downstream Effectors," *Front Immunol.*, 2014; 5: 673; Dolusic et al., "Indoleamine 2,3-dioxygenase inhibitors: A patent review (2008-2012)", *Expert Opin. Ther. Pat.*, 2013, 23(10)), which are each incorporated herein by reference in its entirety. In some embodiments, the IDO1 inhibitor is selected from the compounds of FIG. 1.

Optionally, anti-cancer agents, such as IDO1 inhibitors, may be administered in the form of a pharmaceutically acceptable salt.

Optionally, the IDO1 inhibitor may be administered simultaneously or consecutively with other treatments, such as surgery, radiation, and/or an additional anti-cancer agent in combination. In some cases, synergistic effects resulting from an IDO1 inhibitor and a chemotherapeutic agent have been observed (Muller et al., *Nature Medicine*, March 2005, 11(3):312-319, which is incorporated herein by reference). Because IDO expression helps to create an immunosuppressive microenvironment of tolerance, IDO inhibition can potentially enhance the efficacy of other anti-cancer agents, such as immunotherapies and chemotherapies, as well as radiation therapies. In some embodiments, the anti-cancer agent used in combination is an alkylating agent (such as cyclophosphamide or a platinum compound such as cisplatin), antineoplastic antibiotic (such as doxorubicin), antimetabolite (such as 5-Fluorouracil or methotrexate), mitotic inhibitor (such as a paclitaxel or other taxane, or vinblastine or other vinca alkaloid), signal transduction inhibitor (such as a farnesyl transferase inhibitor (FTI) or rapamycin), or anti-angiogenic agent (such as tetrathiomolybdate or other iron chelator).

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). Anti-cancer agents include but are not limited to those listed in Table 2.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Several examples of chemotherapeutic agents that may be used in conjunction with the imaging constructs of the invention are listed in Table 2.

TABLE 2

Examples of Anti-Cancer Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6 - TG | Nilutamide |
| 6 - Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL - 2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin - 2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |

TABLE 2-continued

Examples of Anti-Cancer Agents

| | |
|---|---|
| Mechlorethamine | MTC |
| Hydrochlorine | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

In the case of cancers, positive clinical outcomes that may result from the methods of the invention that involve treatment include, but are not limited to, alleviation of one or more symptoms of the cancer, diminishment of extent of disease, stabilized (i.e., not worsening) state of disease, delay or slowing of disease progression, amelioration or palliation of the disease state, remission (whether partial or total), whether detectable or undetectable, tumor regression, inhibition of tumor growth, inhibition of tumor metastasis, reduction in cancer cell number, inhibition of cancer cell infiltration into peripheral organs, improved time to disease progression (TTP), improved response rate (RR), prolonged overall survival (OS), prolonged time-to-next-treatment (TNTT), or prolonged time from first progression to next treatment, or a combination of two or more of the foregoing.

As used in this specification, the singular forms "a", "an", and "the" include plural reference unless the context clearly dictates otherwise. Thus, for example, a reference to "a compound" includes more than one such compound. A reference to "a cell" includes more than one such cell, and so forth.

As used herein, the terms "patient", "subject", and "individual" are used interchangeably and are intended to include human and non-human animal species. For example, the subject may be a human or non-human mammal. In some embodiments, the subject is a non-human animal model or veterinary patient. For example, the non-human animal patient may be a mammal, reptile, fish, or amphibian. In some embodiments, the non-human animal is a dog, cat, mouse, rat, guinea pig. In some embodiments, the non-human animal is a primate.

Embodiments of the invention are further illustrated by the following examples. It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Following are examples that illustrate procedures for practicing the invention. These examples should not be construed as limiting. All percentages are by weight and all solvent mixture proportions are by volume unless otherwise noted.

Materials and Methods

All reagents and solvents were purchased from Sigma-Aldrich or Fluka and used as received without further purification. Solid-phase extraction cartridges (Sep-Pak QMA and Sep-Pak C18) were purchased from Water Corp., Milford, Mass., USA. Column chromatography was performed on silica gel (60 Å, 230-400 mesh, for flash chromatography). TLC was performed on aluminum plates pre-coated with silica (200 μm, 60 $F_{254}$), which were visualized either by quenching of ultraviolet fluorescence ($\lambda_{max}$=254 nm) or by iodine stain. 1H and $^{13}$C spectra were obtained on a Varian Mercury 400-MHz spectrometer with $CDCl_3$, MeCN-$d_3$, and DMSO-$d_6$ as the solvent. All coupling constants were measured in hertz (Hz), and the chemical shifts ($\delta_H$ and $\delta_C$) were quoted in parts per million relative to the internal standard tetramethylsilane (δ 0). $^{19}$F chemical shifts were measured with respect to $CFCl_3$. High-resolution mass spectroscopy (HRMS) was carried out on an Agilent 6210 LC-MS (ESI-time of flight).

HPLC analysis and purification were performed on Agilent 1260 using an in-line UV detector (254 nm) and a NaI crystal flow-count radioactivity detector (Lablogic Flow-RAM detector). The analytical HPLC was performed on an Agilent Eclipse XDB C18 column (5 μm, 4.6×250 mm) with the flow rate 1.0 mL/min using MeCN/0.1% acetic acid in $H_2O$ 50/50, 12/88, or 40/60 as an eluent. Semipreparative HPLC purification system was performed on an Agilent Eclipse XDB C18 column (5 m, 9.6×250 mm) with the flow rate 5.0 mL/min using MeCN/0.1% acetic acid in $H_2O$ 40/60 for 20 min. Radio-TLC Imaging Scanner (AR-2000, Bio-Scan USA) was used for the radiochemical purity measurements. A dose calibrator (ATOMLAB 500, Biodex) was used for all radioactivity measurements.

4-Amino-N-hydroxy-1,2,5-oxadiazole-3-carboximidamide (2)

Malononitrile (13.2 g, 200 mmol) was added to preheated water (280 mL, 45° C.) and stirred for 5 min. The resulting solution was cooled in an ice/water bath, and sodium nitrite (15.18 g, 220 mmol) was added and stirred for 5 min. Then, HCl (10 N, 13.2 mL) was added to start the mild exothermic reaction, while bubbles were observed. After 3 min, the ice/water bath was removed, and the reaction mixture was stirred 1.5 h at room temperature. The hydroxylamine (39.6 g, 600 mmol) was added to the light yellow reaction mixture in an ice/water bath. After being stirred at room temperature for 1 h, the reaction mixture was refluxed for 2 h and then cooled in an ice/water bath. HCl (10 N, 32.0 mL) was added in portions to the reaction mixture till neutral (pH=7.0 via a pH meter). The precipitate was collected by filtration, washed well with water, and dried in a vacuum (oil pump) to afford the desired product 2 (26.0 g, 91%).

$R_f$ (ethyl acetate/hexanes: 1/1 (v/v)): 0.22.

$^1$H-NMR (400 MHz, DMSO-$d_6$): δ 10.46 (s, 1 H, OH), 6.27 (s, 2H, $NH_2$), and 6.19 (s, 2H, $NH_2$).

$^{13}$C-NMR (100 MHz, $CD_3OD$): δ 155.86, 145.73, and 141.13.

HRMS Calcd for $C_3H_6N_5O_2Na$ [M+Na]$^+$, 166.0336, found, 166.0337.

4-Amino-N-hydroxy-1,2,5-oxadiazole-3-carboximidoyl chloride (3)

4-Amino-N-hydroxy-1,2,5-oxadiazole-3-carboximidamide (2; 14.31 g, 100 mmol) and NaCl (17.0 g, 290 mmol)

were added to a mixture of water (190 mL), acetic acid (100 mL), and HCl (10M, 50 mL). The suspension was stirred at room temperature till complete solution was achieved and then cooled by an ice/water bath. A solution of sodium nitrite (6.81 g, 98 mmol) in water (24.0 mL) was added, and the reaction mixture was stirred from 0° C. to room temperature overnight. The white precipitate was collected by filtration, washed well with water, taken in ethyl acetate, and dried over anhydrous $Na_2SO_4$. The suspension was filtered, and the filtrate was evaporated on a rotary evaporator to offer the product 3 (9.24 g, 57%).

$^1$H-NMR (400 MHz, DMSO-$d_6$): δ 13.40 (s, 1 H, OH) and 6.29 (s, br, 2H, $NH_2$).

$^{13}$C-NMR (100 MHz, $CD_3OD$): δ 155.21, 142.91, and 129.20.

4-Amino-N-(3-chloro-4-fluorophenyl)-N'-hydroxy-1,2,5-oxadiazole-3-carboximidamide (IDO5L)

4-Amino-N-hydroxy-1,2,5-oxadiazole-3-carboximidoyl chloride (3; 1.63 g, 10.0 mmol) and 3-chloro-4-fluoroaniline (1.60 g, 11.0 mmol) were added in ethanol (40 mL). Then, $NaHCO_3$ (2.10 g, 25.0 mmol) in water (20 mL) was added. The reaction was stirred and heated at 60° C. for 1 h. The reaction mixture was concentrated by a rotary evaporator and dissolved in ethyl acetate (100 mL), after being washed by brine (50 mL) twice and dried over $Na_2SO_4$. After solvent evaporation, the residue was recrystallized in ethyl acetate/hexanes to afford IDO5L (2.38 g, 88%) as a brown solid.

$R_f$ (ethyl acetate/hexanes: 1/1 (v/v)): 0.45.

$^1$H-NMR (400 MHz, DMSO-$d_6$): δ 11.41 (s, br, 1 H), 8.91 (s, br, 1 H), 7.21 (dd, J=9.2 and 9.2 Hz, 1 H), 6.98 (dd, J=6.4 and 2.8 Hz, 1 H), 6.72-6.76 (m, 1 H), and 6.27 (s, 2 H).

$^{13}$C-NMR (100 MHz, DMSO-$d_6$): δ 155.3, 152.2 (d, $J^1_{C-F}$=239.3 Hz), 140.4, 139.3, 137.9 (d, $J^3_{C-F}$=2.9 Hz), 122.0, 120.8 (d, $J^3_{C-F}$=6.8 Hz), 118.7 (d, $J^2_{C-F}$=18.5 Hz), and 116.2 (d, $J^2_{C-F}$=21.7 Hz).

HRMS calculated for $C_9H_8ClFN_5O_2[M+H]^-$: m/z=272.0345, found 272.0340.

2-Chloro-N,N-dimethyl-4-nitroaniline (5)

2-Chloro-4-nitroaniline 4 (5.18 g, 30.0 mmol) in 60 mL anhydrous THF was added to 60% NaH (60%, 2.64 g, 66.0 mmol) under argon protection at 0° C. The resulting solution was stirred in an ice/water bath for 10 min and then stirred for 30 min at room temperature. Methyl iodide (10.65 g, 75.0 mmol) was added to the reaction mixture and stirred for 17 h at room temperature. Then, ice (~10.0 g) and water (40 mL) were added to the reaction mixture to quench the reaction. After 5 min, the organic solvent was removed by vacuum. The aqueous layer was extracted by ethyl acetate (3×100 mL), and the combined organic layer was washed by brine (100 mL) and dried over anhydrous $Na_2SO_4$. After solvent evaporation, the resulting residue was purified by flash chromatography ($SiO_2$) and eluted with ethyl acetate/hexanes (1/19, v/v) to afford 5 (4.73 g, 79%) as a yellow solid.

$R_f$ (ethyl acetate/hexanes: 1/19 (v/v)): 0.20.

$^1$H-NMR (400 MHz, $CDCl_3$): δ 8.18 (d, J=2.8 Hz, 1H, Ar—H), 8.03 (dd, J=9.2 and 2.8 Hz, 1H, Ar—H), 6.96 (d, J=8.8 Hz, 1H, Ar—H), and 3.01 (s, 6H, $N(CH_3)_2$).

$^{13}$C-NMR (100 MHz, $CDCl_3$): δ 155.4, 140.6, 127.1, 124.7, 123.3, 117.8, and 43.0.

HRMS calculated for $C_8H_9ClN_2O_2[M+H]^+$: m/z=201.0425, found 201.0433.

2-chloro-N,N,N-trimethyl-4-nitrobenzenaminium trifluoromethanesulfonate (6)

To a solution of 2-chloro-N,N-dimethyl-4-nitroaniline (0.60 g, 3.0 mmol) in anhydrous dichloromethane (20 mL), methyl trifluoromethanesulfonate (0.99 g, 6.0 mmol) was added under argon protection at room temperature. The resulting red solution was stirred for 24 h at room temperature, and precipitation was observed. The off-white precipitate was collected by filtration and washed well with dichloromethane (3×20 mL) and ethyl ether (20 mL). The precipitate was then evaporated on a rotary evaporator and dried by vacuum to offer off the product 6 (1.09 g, 76%) as a white solid.

$^1$H-NMR (400 MHz, DMSO-$d_6$): δ 8.60 (d, J=2.4 Hz, 1 H, Ar—H), 8.41 (dd, J=9.2 and 2.4 Hz, 1 H, Ar—H), 8.34 (d, J=9.2 Hz, 1 H, Ar—H), and 3.85 (s, 9 H, $N(CH_3)_3$).

$^{13}$C-NMR (100 MHz, DMSO-$d_6$): δ 148.7, 146.3, 129.3, 127.7, 126.5, 124.1, 121.1 (q, $J^1_{C-F}$=320.2 Hz, $CF_3$), and 56.2.

HRMS calculated for $C_9H_{12}ClN_2O_2[M]+$: m/z=215.0587, found 215.0587.

2-chloro-N1,N1-dimethylbenzene-1,4-diamine (7)

2-Chloro-N,N-dimethyl-4-nitroaniline 5 (3.00 g, 15.0 mmol) in methanol (50 mL) was added with palladium on activated charcoal (42 mg). Then, $NaBH_4$ (1.14 g, 30.0 mmol) was added to the solution dropwise under stirring at room temperature. Determine reaction completeness by TLC (silica, ethyl acetate/hexanes=1:2, UV light and $I_2$ stain). When completed (~1 h), cold HCl solution (2 N, 20 mL) was added dropwise to the mixture to quench the reaction (caution: hydrogen gas bubble generated). The reaction solvent was removed by rotary evaporation. Then, saturated $NaHCO_3$ solution (100 mL) was added, and the resultant aqueous solution was extracted by ethyl acetate (3×50 mL). The combined organic layer was washed by brine (50 mL) and dried over $Na_2SO_4$. After solvent evaporation, the resulting residue was purified by flash chromatography ($SiO_2$) and eluted with ethyl acetate/hexanes (1/2, v/v) to afford the product 7 (2.54 g, 99%) as a black solid.

$R_f$ (ethyl acetate/hexanes: 1/2 (v/v)): 0.40.

$^1$H-NMR (400 MHz, $CDCl_3$): δ 6.92 (d, J=8.4 Hz, 1H, Ar—H), 6.71 (d, J=2.8 Hz, 1H, Ar—H), 6.53 (dd, J=8.4 and 2.8 Hz, 1H, Ar—H), 3.54 (s, 2H, $NH_2$), and 2.70 (s, 6H, $NCH_3$).

$^{13}$C-NMR (100 MHz, $CDCl_3$): δ 142.8, 142.0, 129.5, 121.1, 117.0, 114.2, and 44.5.

HRMS calculated for $C_8H_{11}ClN_2$ $[M+H]^+$: m/z=171.0684, found 171.0678.

4-Amino-N-(3-chloro-4-(dimethylamino)phenyl)-N'-hydroxy-1,2,5-oxadiazole-3-carboximidamide (8)

2-Chloro-N1,N1-dimethylbenzene-1,4-diamine 7 (1.79 g, 10.5 mmol) and 4-amino-N-hydroxy-1,2,5-oxadiazole-3-carboximidoyl chloride 3 (1.63 g, 10 mmol) in ethanol (50 mL) were added in $NaHCO_3$ solution (2.01 g $NaHCO_3$ in 25 mL $H_2O$). The reaction mixture was stirred at 60° C. for 30 min, and the reaction completeness was determined by TLC. After being extracted by ethyl acetate (2×50 mL), the combined organic layer was washed by brine (50 mL) and dried over anhydrous $Na_2SO_4$. After solvent evaporation, the resulting residue was purified by flash chromatography ($SiO_2$) and eluted with ethyl acetate/hexanes (3/7, v/v) to afford the product 8 (2.85 g, 96%) as a gray solid.

R$_f$ (ethyl acetate/hexanes: 3/7 (v/v)): 0.37.

$^1$H-NMR (400 MHz, DMSO-d$_6$): δ 11.23 (s, 1H, OH), 8.65 (s, 1H, NH), 6.92 (d, J=8.4 Hz, 1H, Ar—H), 6.83 (d, J=2.4 Hz, 1H, Ar—H), 6.59 (dd, J=8.4 and 2.4 Hz, 1H, Ar—H), 6.20 (s, 2H, NH$_2$), and 2.57 (s, 6 H, N(CH$_3$)$_2$).

$^{13}$C-NMR (100 MHz, DMSO-d$_6$): δ 155.4, 144.8, 140.5, 139.6, 136.1, 126.9, 122.8, 120.4, 120.1, and 43.6.

HRMS calculated for C$_{11}$H$_{13}$ClN$_6$O$_2$[M+H]$^+$: m/z=297.0861, found 297.0872.

3-(4-Amino-1,2,5-oxadiazol-3-yl)-4-(3-chloro-4-(dimethylamino)phenyl)-1,2,4-oxadiazol-5(4H)-one (9)

4-Amino-N-(3-chloro-4-(dimethylamino)phenyl)-N'-hydroxy-1,2,5-oxadiazole-3-carboximidamide 8 (0.864 g, 2.91 mmol) and 1,1'-carbonyldiimidazole (0.519 g, 3.20 mmol) in THF (10 mL) were stirred at 70° C. for 1 h. The reaction completeness was determined by TLC. After solvent evaporation, the resulting residue was purified by chromatography (SiO$_2$) to afford the product 9 (0.866 g, 92%) as a gray solid.

R$_f$ (ethyl acetate/hexanes: 3/7 (v/v)): 0.26.

$^1$H-NMR (400 MHz, DMSO-d$_6$): δ 7.68 (d, J=2.4 Hz, 1H, Ar—H), 7.47 (dd, J=8.8 and 2.4 Hz, 1H, Ar—H), 7.23 (d, J=8.8 Hz, 1H, Ar—H), 6.61 (s, 2H, NH$_2$), and 2.79 (s, 6 H, N(CH$_3$)$_2$).

$^{13}$C-NMR (100 MHz, DMSO-d$_6$): δ 157.1, 155.3, 151.4, 149.1, 134.3, 129.9, 127.6, 125.9, 125.2, 120.3, and 43.0.

HRMS calculated for C$_{12}$H$_{11}$ClN$_6$O$_3$[M+H]$^+$: m/z=323.0654, found 323.0662.

4-(3-(4-Amino-1,2,5-oxadiazol-3-yl)-5-oxo-1,2,4-oxadiazol-4(5H)-yl)-2-chloro-N,N,N-trimethylbenzenaminiumtrifluoromethanesulfonate (10)

To a solution of the 3-(4-amino-1,2,5-oxadiazol-3-yl)-4-(3-chloro-4-(dimethylamino)phenyl)-1,2,4-oxadiazol-5(4H)-one 9 (0.806 g, 2.50 mmol) in dichloromethane (30 mL), methyl trifluoromethanesulfonate (548 µL, 5.0 mmol) was added under the protection of nitrogen gas. After being stirred at room temperature overnight (~12 h), the reaction mixture was filtered, and the resulting solid was washed by dichloromethane. The powder was then dissolved in methanol and precipitated by ethyl ether to afford the product 10 (1.00 g, 82%) as a white solid.

$^1$H-NMR (400 MHz, DMSO-d$_6$): δ 8.32 (d, J=8.8 Hz, 1H, Ar—H), 8.17 (d, J=2.4 Hz, 1H, Ar—H), 7.92 (dd, J=8.8 and 2.4 Hz, 1H, Ar—H), 6.67 (s, 2H, NH$_2$), and 3.85 (s, 9H, NCH$_3$).

$^{13}$C-NMR (100 MHz, DMSO-d$_6$): δ 156.8, 155.7, 148.9, 142.8, 134.7, 134.4, 133.7, 129.1, 126.4, 125.9, 121.1 (q, J$^1_{C-F}$=320.3 Hz, CF$_3$), and 56.2. HRMS calculated for C$_{13}$H$_{14}$ClN$_6$O$_3$[M]+: m/z=337.0810, found 337.0796.

Synthesis of [$^{18}$F]11

Aqueous [$^{18}$F]fluoride (1.0-2.0 mL, 5-20 mCi, from Cardinal Health) was trapped on a preconditioning QMA cartridge and eluted with a mixture of Kryptofix [2.2.2] (475 µL of a 23-mg/mL stock solution in MeCN) and K$_2$CO$_3$ stock solution (25 µL of a 400-mg/mL stock solution in water). [$^{18}$F]Fluoride was dried at 120° C. under a stream of nitrogen by azeotropic distillation with anhydrous acetonitrile (3×0.3 mL) to give the no-carrier-added [K/K$_{222}$]$^{+18}$F$^-$ complex as a white semisolid residue. After cooling to room temperature, a solution of triflate precursor 6 (3.6 mg, 10 mol) in anhydrous acetonitrile (0.5 mL) was added into the reaction vial. After being heated at 70° C. for 5 min, the mixture was mixed with water (4.0 mL), and the aqueous solution was passed through an activated C18 Sep-Pak (pretreated by passing through 5 mL of methanol, 10 mL of water and 40 mL of air). The Sep-Pak was rinsed with 10% acetonitrile in water (5.0 mL), and the residue solvent was partly removed by air (20 mL). The product 2-chloro-4-[$^{18}$F]fluoronitrobenzene ([$^{18}$F]11) was slowly eluted through the column with methanol (1.5 mL). Radio-TLC analysis of the crude reaction mixture showed 98% radiochemical yield (EtOAc/hexanes: 1/3 (v/v), R$_f$=0.80) with unreacted [$^{18}$F] fluoride as the main impurity.

Synthesis of [$^{18}$F]12

The elution from the previous step was collected in a reaction vial containing Pd/C (1 mg) and NaBH$_4$ (5 mg) under nitrogen protection. The reaction mixture was stirred at room temperature for 5 min before being quenched by concentrated HCl (25 L). After filtering off the catalyst, the solution was concentrated at 100° C. under a stream of nitrogen in 15 min. Radio-TLC analysis of the crude reaction mixture showed 89-96% conversion to product (EtOAc/hexanes: 1/3 (v/v), R$_f$=0.34).

Synthesis of [$^{18}$F]IDO5L

The residue of [$^{18}$F]12 was redissolved in 200 µL of methanol and then mixed with NaHCO$_3$ solution (300 µL, 1 M). The acidity of the resulting mixture was examined by a pH paper to confirm pH ~9. A solution of 4-amino-N-hydroxy-1,2,5-oxadiazole-3-carboximidamidoyl chloride 3 (3.2 mg, 20 µmol) in methanol (200 µL) was added, and the reaction mixture was stirred at 60° C. for 15 min. Radio-TLC analysis of the crude reaction mixture showed 51-64% conversion to [$^{18}$F]IDO5L (EtOAc/hexanes: 1/1 (v/v), R$_f$=0.45). The solution was subsequently filtered, and the filter was washed with methanol (200 µL). The methanol solution was purified by HPLC with retention time of 11 min. The collected HPLC fraction (~4 mL) was diluted with water and then passed through the activated C18 Sep-Pak column. After being washed by 10 mL of water, the labeled product was eluted by 1.5 mL methanol and dried under a stream of nitrogen in 100° C. Finally, the residue was dissolved in 0.3 mL physiological saline for animal study. Radiochemical purity and specific activity of the product [$^{18}$F]IDO5L were determined by analytical HPLC with the retention time of 13.5 min. The identity of [$^{18}$F]IDO5L was confirmed by a coinjection with a nonradioactive standard IDO5L. Typically, starting from 0.34 to 0.74 GBq (9.2-19.9 mCi) [$^{18}$F]fluoride, 35 to 77 MBq (0.94-2.09 mCi) of purified [$^{18}$F]IDO5L could be obtained in ~90 min.

EXAMPLE 1

Chemistry

The reference compound IDO5L (4-amino-N-(3-chloro-4-fluorophenyl)-N'-hydroxy-1,2,5-oxadiazole-3-carboximidamide) was synthesized using the reported three-step method with minor modification, which is illustrated in Scheme 2 [14]. Firstly, malononitrile was treated with hydroxylamine, sodium nitrite, and hydrochloric acid to give hydroxyamidine 2 in 91% yield. The hydroxyamidine 2 was then diazotized under acidic conditions to provide the hydroximoyl chloride 2 in 57% yield. Coupling of compound 2 with 3-chloro-4-fluoroaniline was carried in the basic conditions to produce IDO5L as brown powder in the yield of 88%.

The synthesis of the two triflate precursors 6 and 10 started from commercially available 2-chloro-4-nitroaniline 4 (Scheme 3). Aniline 4 was deprotonated by sodium hydride followed by methylation to afford 2-chloro-N,N-dimethyl-4-nitroaniline 5 in 79% yield. After further methylation of compound 5, the triflate precursor 6 was obtained in 76% yield. To produce another triflate precursor 10, the nitro group of compound 5 was firstly reduced to aniline 7 in 99% yield by sodium borohydrate under the catalysis of palladium on activated charcoal [15]. Compound 8 was then achieved by coupling aniline 7 and compound 3 in 96% yield under the basic conditions. The N-hydroxyamidine group of compound 8 was then cyclized with 1,1'-carbonyldiimidazole to give compound 9 in 92% yield. Finally, compound 9 was methylated by methyl trifluoromethanesulfonate to produce the triflate 10 in the yield of 82%.

Scheme 2. Synthesis of standard IDO5L.

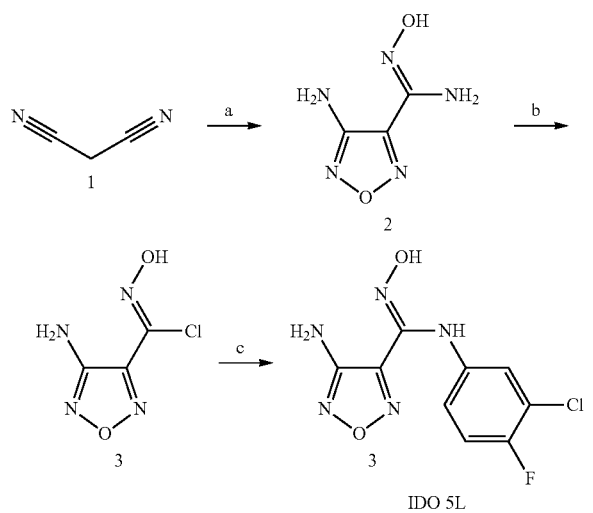

Conditions: (a) NaNO$_2$, HCl (aq.) 2N; then, 50% NH$_2$OH relfux, 2 h; HCl 10N to pH = 7.0, 91%; (b) NaNO$_2$, HCl, H$_2$O, 0° C., 1.5 h, 57%; and (c) 3-chloro-4-fluoroaniline, NaHCO$_3$, EtOH, room temperature (RT.) to 60° C., 1 h, 88%.

Scheme 3. Synthesis of two triflate precursors 6 and 10.

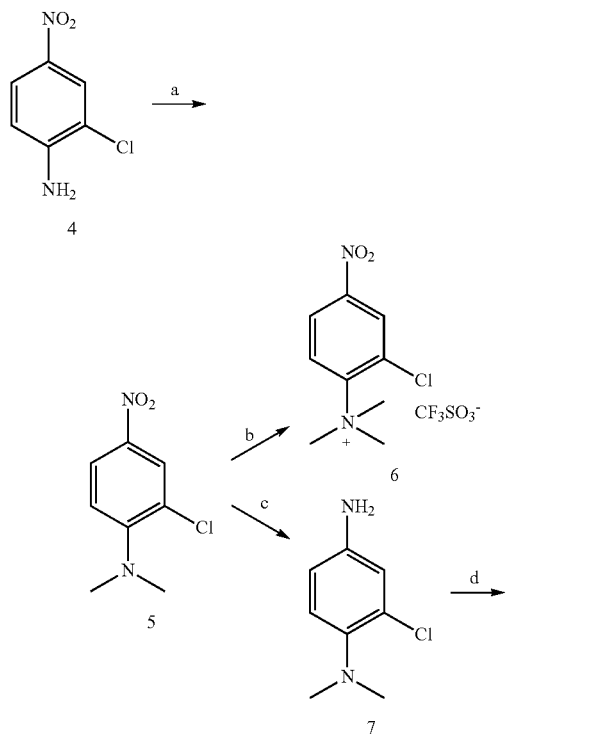

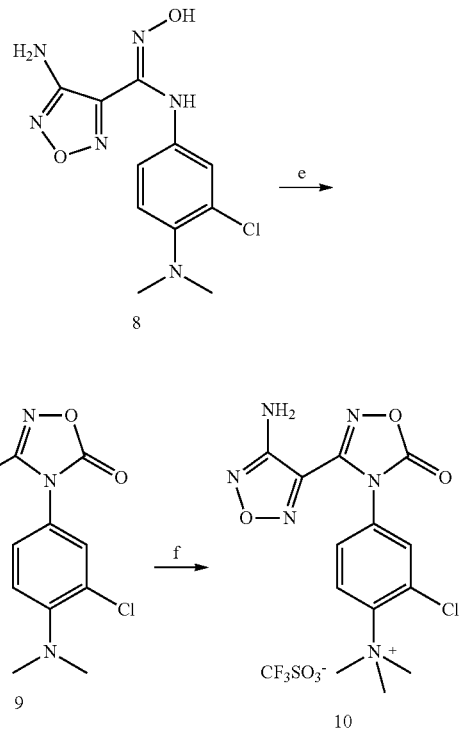

Conditions: (a) NaH, THF, 0° C. to RT., 30 min and then MeI 17 h, 79%; (b) methyl trifluoromethanesulfonate, dichloromethane, RT., 24 h, 76%; (c) NaBH$_4$, Pd/C, MeOH, RT. 1 h, 99%; (d) compound 3, NaHCO$_3$, ethanol, H$_2$O, 60° C., 30 min, 96%; (e) 1,1'-carbonyldiimidazole, THF, 70° C., 1 h, 92%; and (f) methyl trifluoromethanesulfonate, dichloromethane, RT., 12 h, 82%.

EXAMPLE 2

Radiochemistry

Because it is attractive as a one-step radiolabeling procedure, aryltrimethylammonium was often used by many as a leaving group in the nucleophilic substitution of no-carrier-added [$^{18}$F] fluoride, the triflate precursor, can be used for $^{18}$F-labeling strategy to replace the conventional complex and long process of multiple-step radiolabeling procedure, which shortens reaction time and labor significantly. The synthesis of the target tracer $^{18}$F-IDO5L (Scheme 4) was performed initially by the conventional Kryptofix-mediated nucleophilic $^{18}$F-substitution of triflate precursor 10 followed by NaOH hydrolysis. However, not $^{18}$F-IDO5L but unlabeled $^{18}$F anion was observed in the radio-HPLC profiles of the reaction mixture under various reaction conditions such as different solvents (dimethyl sulfoxide (DMSO)/MeCN), temperature (90° C./120° C.), and reaction time (5-30 min). Analysis of reaction samples before NaOH hydrolysis found that the precursor 10 decomposed to compound 8 and compound 9 as well as other unknown compounds.

Scheme 4. Radiosynthesis of [18F]-IDO5L.

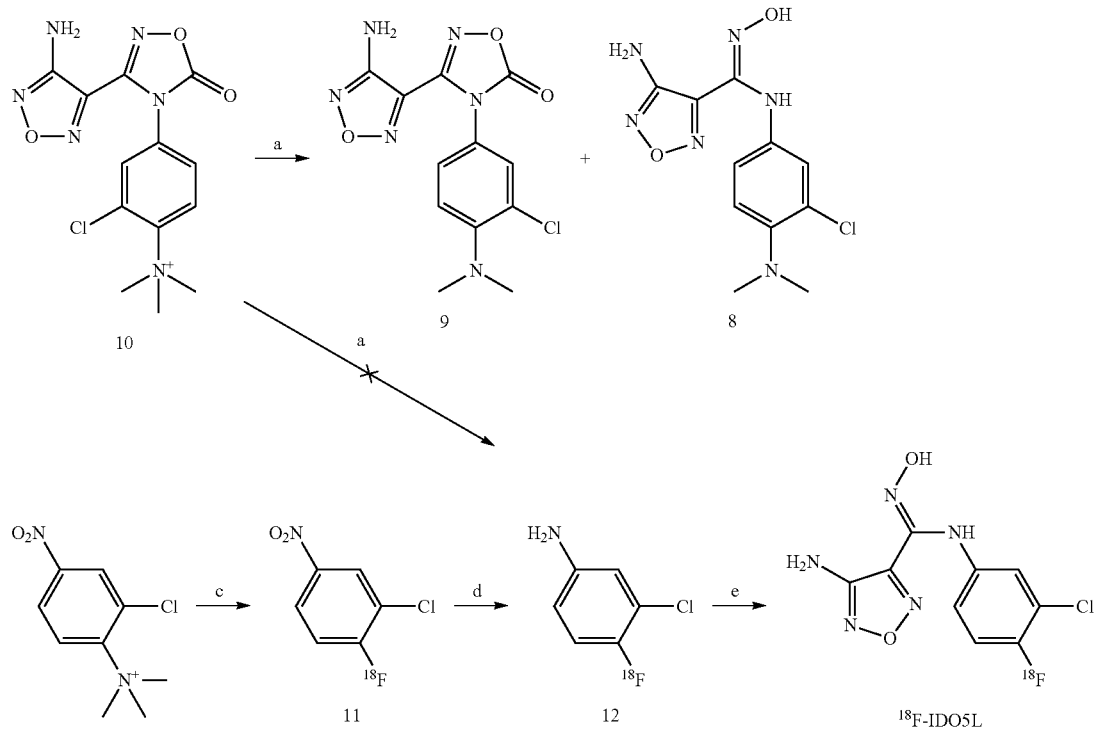

Conditions: (a) [18F]KF/K222, MeCN, RT., 120° C., 30 min, then NaOH (aq.) 1N, 15 min; (b) [18F]KF/K222, MeCN, 70° C., 5 min; (c) NaBH4, Pd/C, MeOH, 70° C., 5 min and (d) compound 3, NaHCO3 (aq.), methanol, 60° C., 15 min.

Considering that the target product IDO5L is stable under the labeling conditions, it was hypothesized that the failure of labeling is because of the difficulty of nucleophilic aromatic fluorination on the weak activated aromatic ring and the ease of decomposition of the carboximidamide protection group and trimethylammonium triflate salts 10.

Figure 2A:
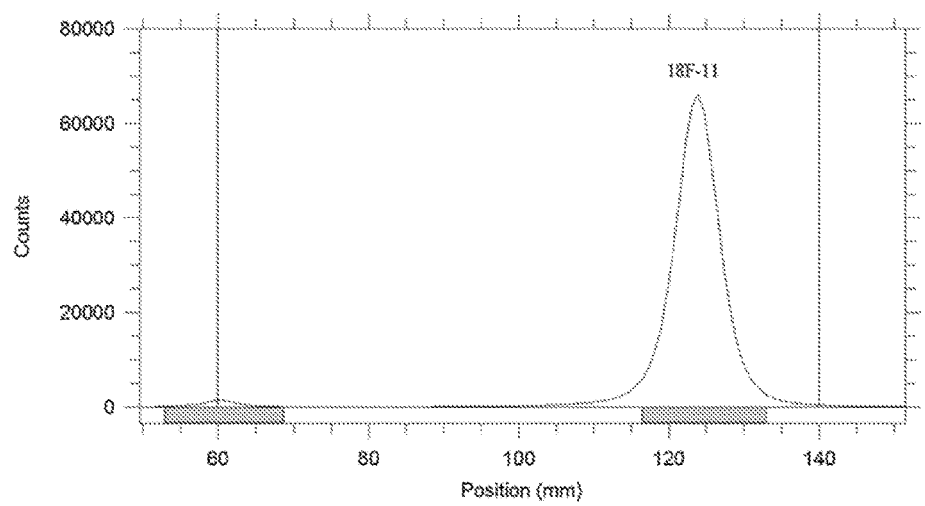
FIGS. 2A-2C. Representative radio-TLC profiles of (FIG. 2A) crude sample of $^{18}$F-11 (EtOAc/hexanes=1:3, $R_f$=0.80), (FIG. 2B) crude sample of $^{18}$F-12 (EtOAc/hexanes=1:3, $R_f$=0.34), and (FIG. 2C) crude sample of $^{18}$F-IDO5L (EtOAc/hexanes=1:3, $R_f$=0.45).

Although attractive as a one-step radiolabeling procedure, the triflate precursor failed to give the target [18F]IDO5L. Consequently, a three-step radiochemical route has been established by using [18F]-labeled aniline as intermediate (Scheme 4). The 3-chloro-4-[18F]fluoroaniline intermediate was synthesized using the reported two-step method with minor modification [15,16]. The first step involved the nucleophilic aromatic substitution of triflate precursor 6 by Kryptofix 222/K2CO3-activated [18F] in acetonitrile. After optimization, the labeling reaction was completed in 5 min with 98% labeling yield (determined by radio-thin-layer chromatography (TLC)) at 70° C. (FIG. 2A). Compared with the reported labeling conditions (room temperature in 25 min) [15], our method saved 20-min reaction time while still achieved good labeling yield. The solvent and reagents used in nucleophilic aromatic substitution were removed by solid-phase extraction on C18 Sep-Pak.

Figure 2B:
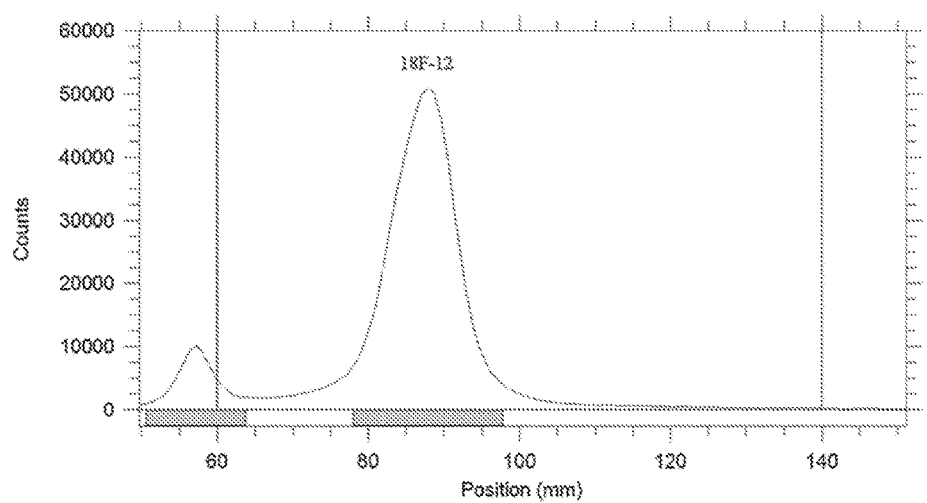

Next, the nitro group of 18F-11 was reduced by sodium borohydrate under the catalysis of palladium on activated charcoal and constant stirring at room temperature for 5 min to afford 18F-12 in 89-96% labeling yield determined by radio-TLC (FIG. 2B). It is worth to mention that relatively lower labeling yield (49-60%) was observed without using stirrer because of poor mixing of reactant and catalyst (Table 3). The excess NaBH4 was quenched by concentrated hydrochloric acid, and the reaction mixture was passed through 0.2-μm filter to remove Pd/C. After being dried at 100° C. under a stream of nitrogen, the residue 18F-12 was redissolved in methanol. The overall radiochemical yields (decay corrected, based on starting [18F]fluoride) are 47-64%, which is less than the reported yield (58-72%) [15], possibly because ~25% activity was volatilized during the solvent removal process.

TABLE 3

Labeling yields of each reaction step

| Product | Time (min) | Conditions | Labeling yield* |
|---|---|---|---|
| 18F-11 | 2 | | 94 |
| | 5 | | 98 |
| | 10 | | 98 |
| 18F-12 | 5 | No stirrer | 49-60 (n > 3) |
| | 5 | With stirrer | 89-98 (n > 3) |
| 18F-IDO5L | 15 | Et3N (0.7 mmol, 35 eq.)† | 0 (n = 3) |
| | 15 | NaHCO3 (aq.; 0.3 mmol, 15 eq.)† | 51-64 (n > 3) |
| | 15 | Na2CO3 (aq.; 0.15 mmol, 7.5 eq.)† | 20-40 (n > 3) |

*By radio-TLC, n = 1 unless otherwise stated
†By radio-TLC, n = 1 unless otherwise stated. B. eq. equivalent of compound 3

Figure 2C:
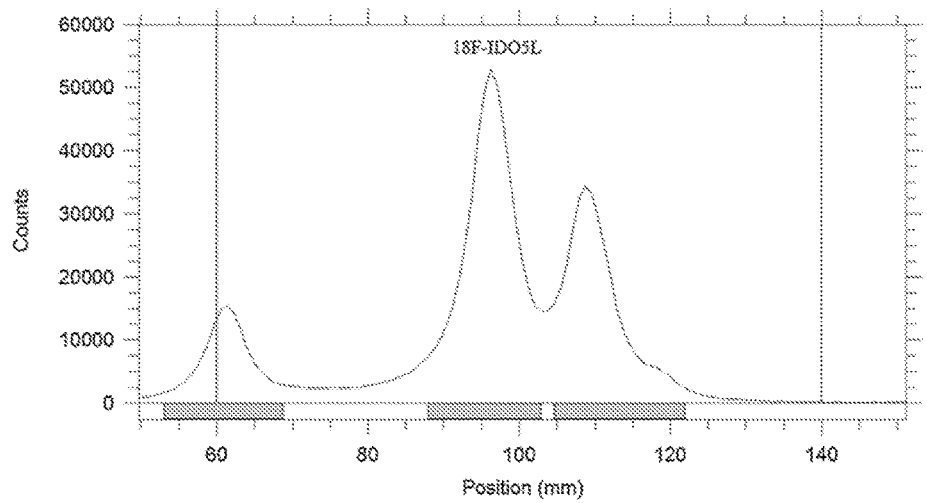
Figures 3A, 3B:
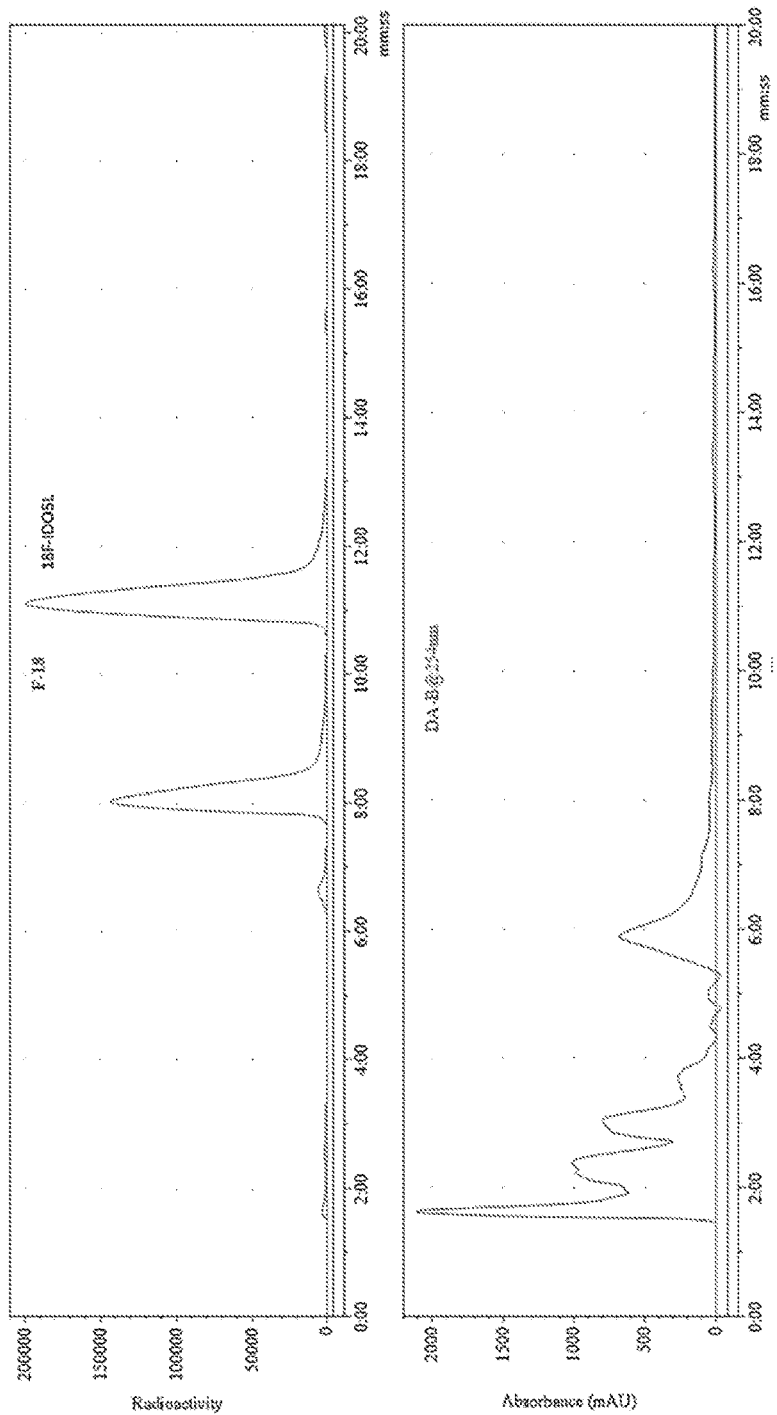
FIGS. 3A-3B. Representative chromatogram from the preparative HPLC separation of the $^{18}$F-IDO5L product.
Figures 4A, 4B:
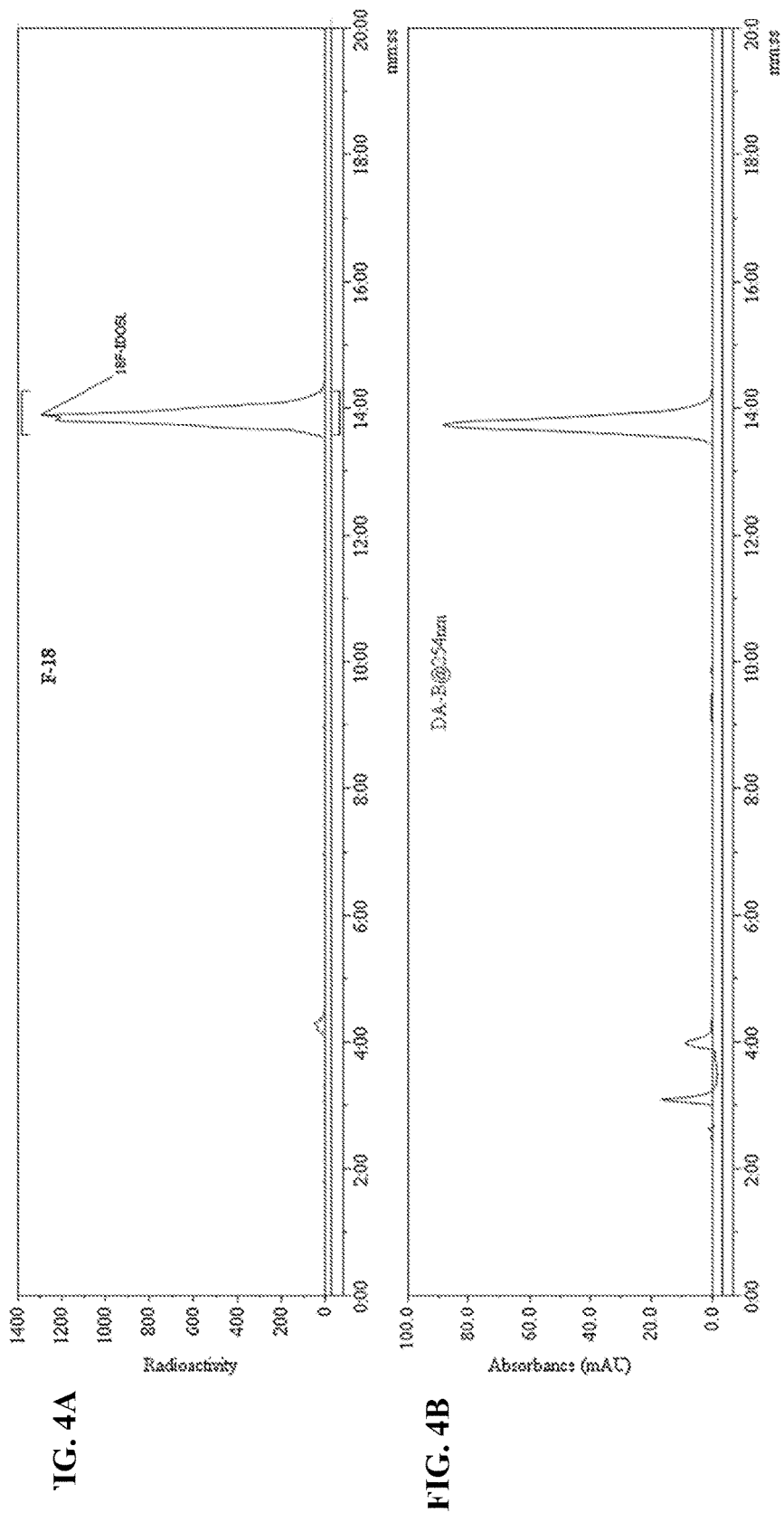
FIGS. 4A-4B. Representative chromatogram from the HPLC analysis of the purified $^{18}$F-IDO5L, co-injection with reference IDO5L.
Figure 5:
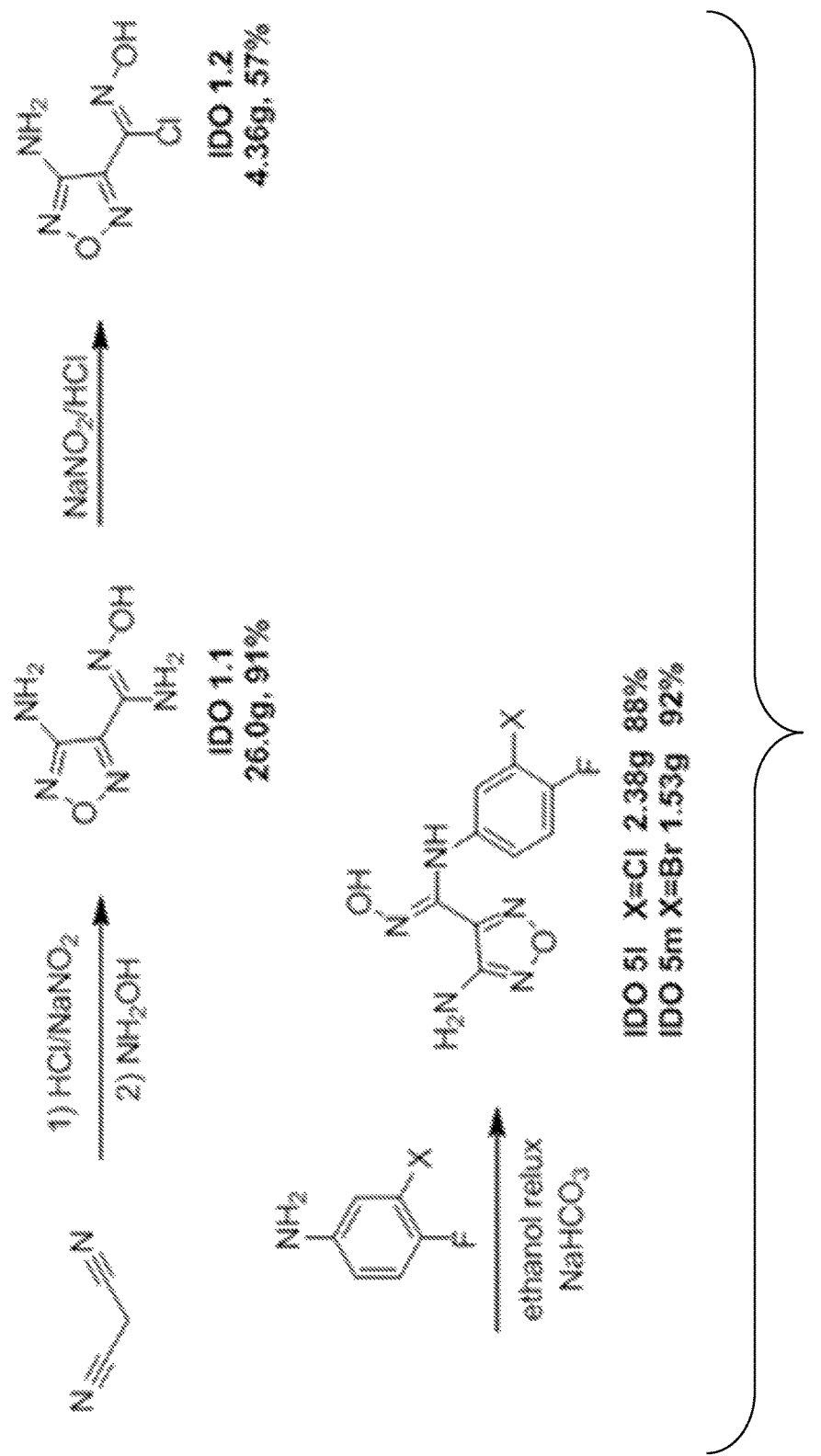
FIG. 5. Synthesis of IDO5L (wherein X=chlorine) and IDO5M (wherein X=bromine).
Figures 6A, 6B:
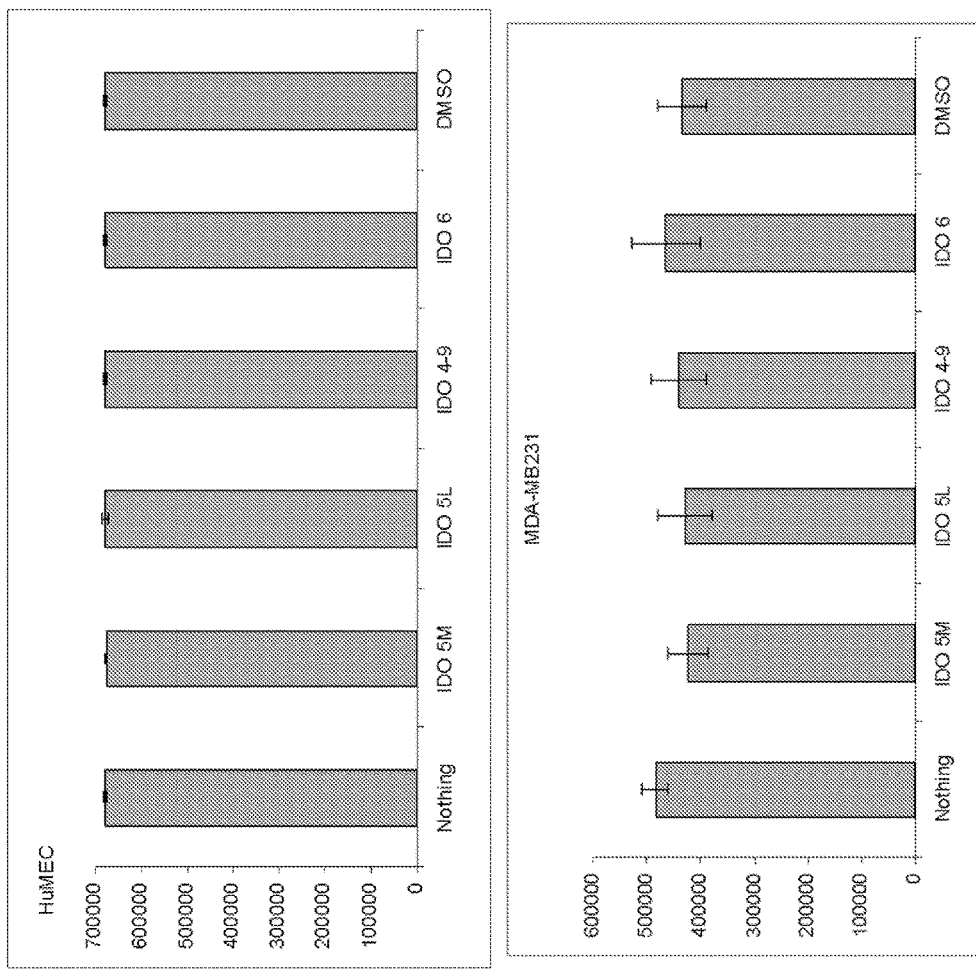
FIGS. 6A-6C. Cell viability study of HuMEC cells, MCA-MB-231 cells, and Hela cells, respectively, incubated with 100 nM of IDO inhibitors. After 2 days of incubation, alamarBlue cell viability reagent was added to cells and the fluorescence intensity (arbitrary fluorescent units) was measured after 3 hours incubation (n=4). Cytotoxicity of four IDO inhibitors toward different cell lines was evaluated with a cell proliferation assay using alamarBlue cell viability reagent. Hela cells were cultured in EMEM medium (ATCC 30-2003) containing 10% FBS, MDA-MB-231 and MCF-7 were cultured in RPMI-1640 Medium containing 10% FBS, while HuMEC cells were cultured in HuMEC medium (ATCC 12752-010). The cell proliferation assay included the following: harvesting of the cells by trypsinization and adding culture media to adjust to 10000 cell/mL; add 0.2 mL of cell suspension to each well and incubated at 37° C. in 5% $CO_2$ atmosphere for 2 days; adding 1 μL of inhibitor solution (0.1 mM in DMSO) into growth media (1 mL) to get growth media w/inhibitor; aspirating spent growth medium from the wells and adding 200 μL of growth media w/ inhibitors and incubating at 37° C. in 5% $CO_2$ atmosphere for 2 days; adding 20 μL of the alamarBlue (Invitrogen) into each well; incubating for addition 3 hours at 37° C. in 5% $CO_2$ atmosphere; and reading the fluorescence intensity of each well with a plate reader (excitation, 544 nm; Emission 595 nm). The fluorescent signal is linear to the number of living cells.
Figure 6C:
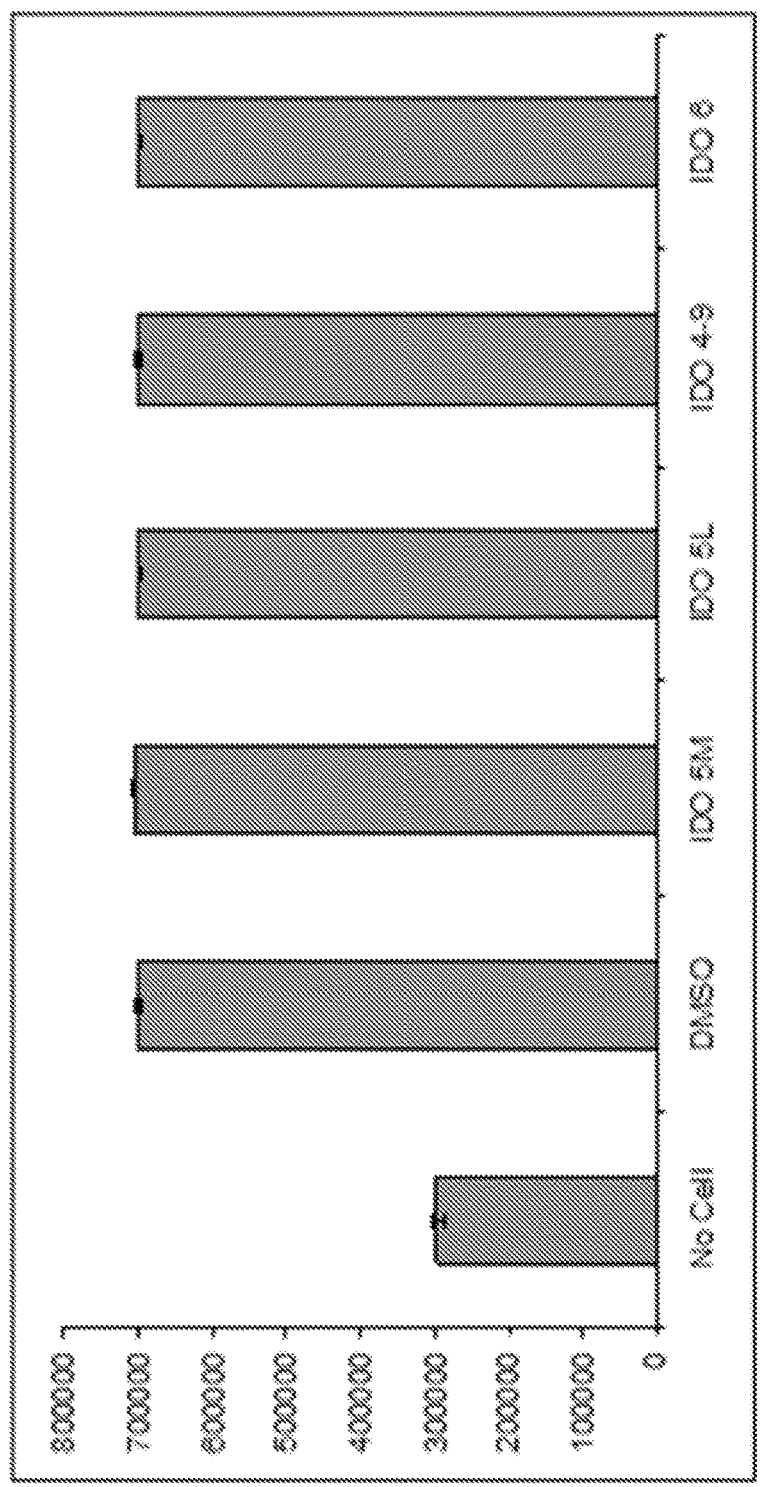
Figure 8:
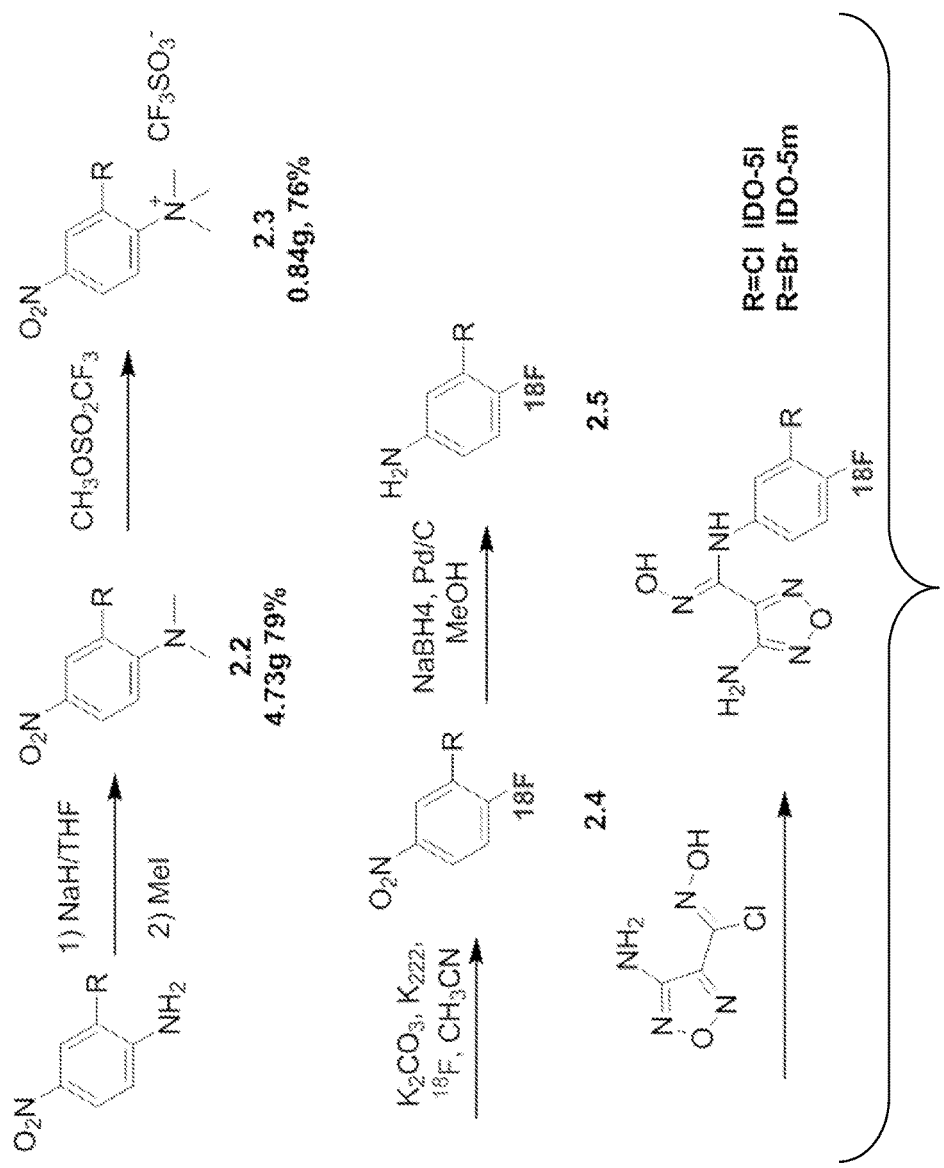
FIG. 8. Synthesis of 18F-IDO5L (wherein R=chlorine) and 18F-IDO5M (wherein R=bromine).
Figure 9:
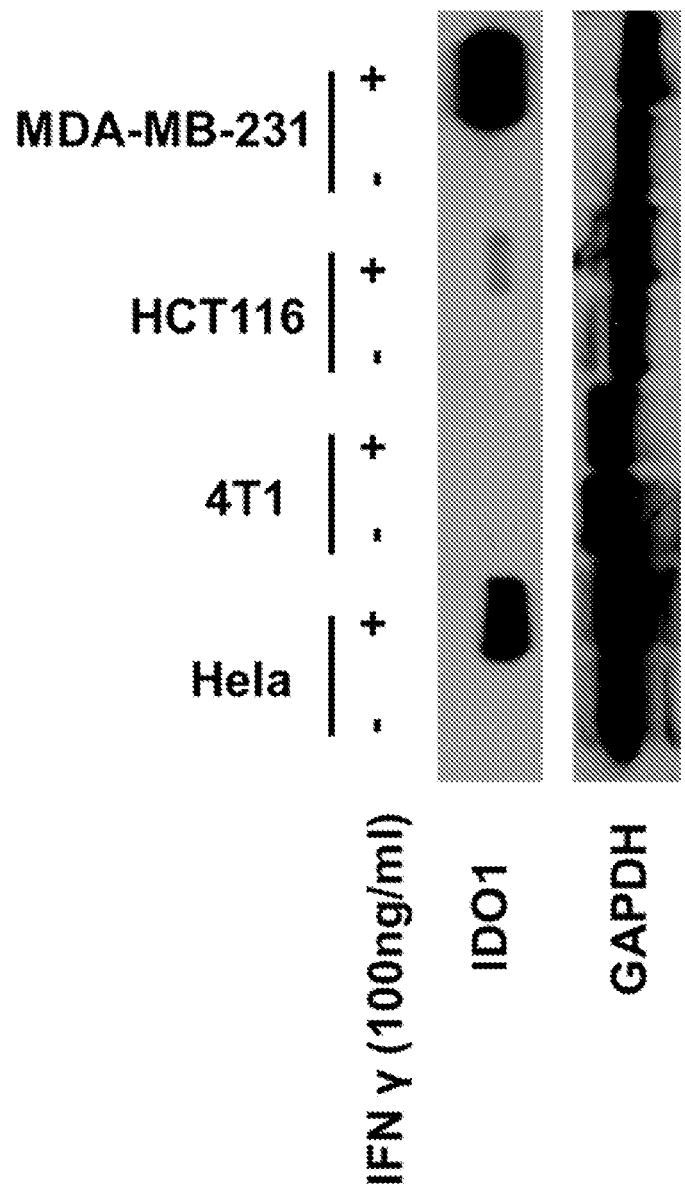
FIG. 9. Expression of IDO1 in four cell lines. Hela, 4T1, HCT116 and MDA-MB-231 cells were seeded in 6-well plates. After being grown overnight, IFN-γ (100 ng/ml) were added into cells for another 48 hours of incubation. Next, the cells were harvested and the total protein was extracted for the Western blot analysis.
Figure 10B:
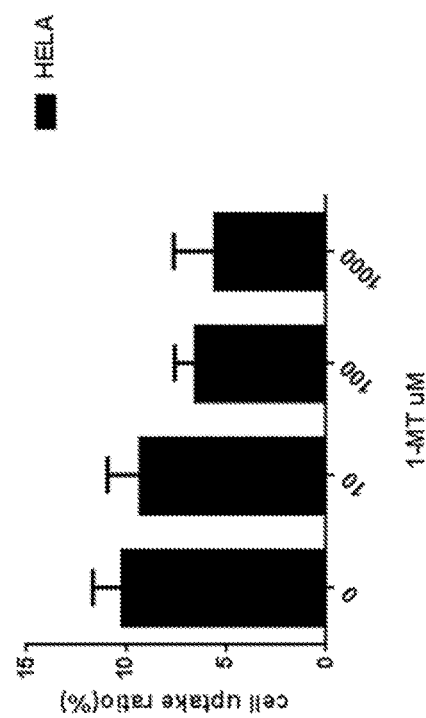
FIGS. 10A-10B. Cell uptake assay (each data point reflects the mean value of n≥3, error bars show standard deviation from the mean). Cells were seeded in 96-well plates, after grown overnight, IFN γ (100 ng/ml) and/or serial dilutions of 1-L-MT in 500 μl culture medium were added into cells for another 48 hours of incubation. Next, cell uptake assay was performed as described previously in Chaofeng Huang et al., *Nucl Med Biol*. 2013 May; 4094: 498-506.
Figure 10A:
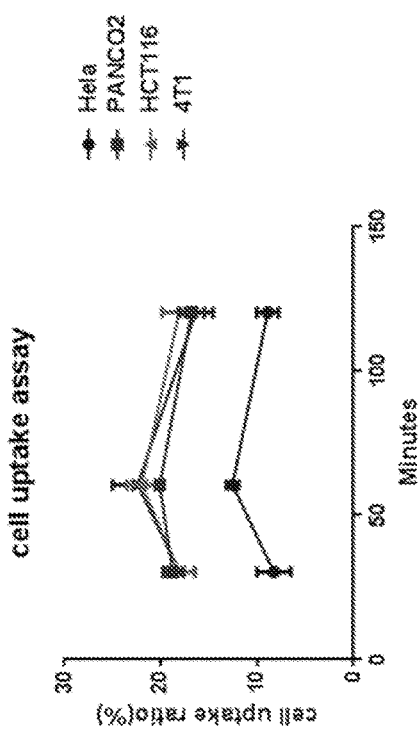
Figure 11:
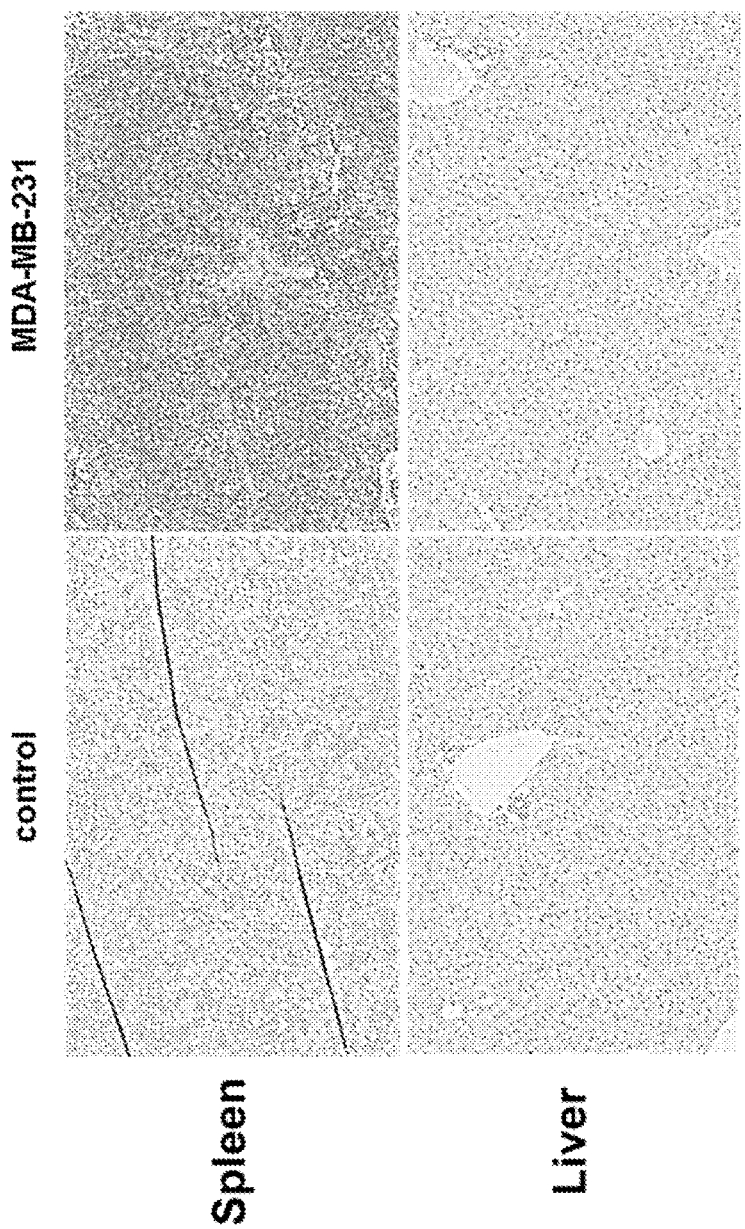
FIG. 11. Immunohistochemistry staining of IDO1 in spleen and liver tissues from MDA-MB-231 xenografts of nude mouse and wild-type mouse. These data show that IDO is highly expressed in spleen of MDA-MB-231 tumor models compared with that of wild-type mouse. These results are in accordance with the targeting IDO PET-CT imaging in MDA-MB-231 tumor models.
Figure 12C:
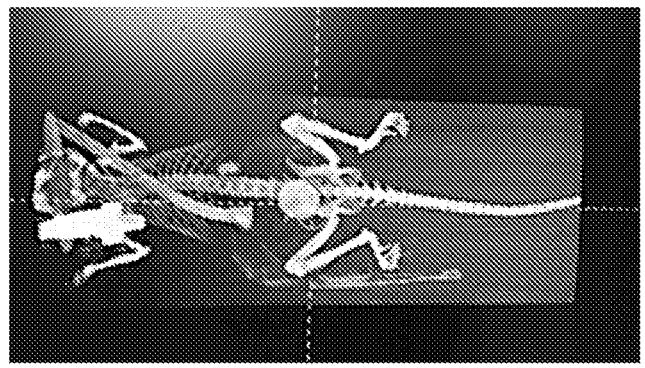
FIGS. 12A-12C. $^{18}$F-IDO5L as novel probes for detection of tumor IDO expression. $^{18F}$IDO5L microPET/CT distinguishes IDO-positive chronic lymphocytic leukemia (CLL) mouse model and wild-type mouse in vivo, in comparison with $^{18}$FDG responses in a CLL mouse model.
Figure 12B:
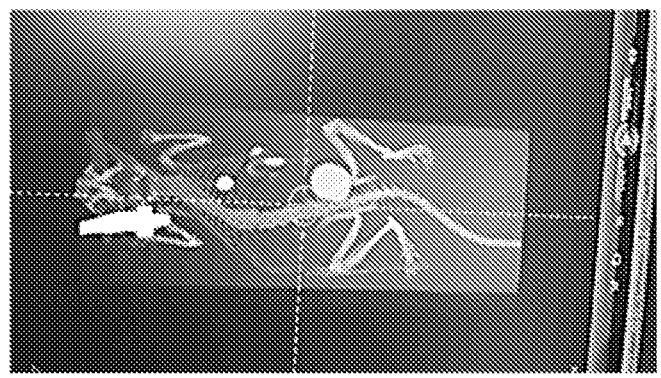
Figure 12A:
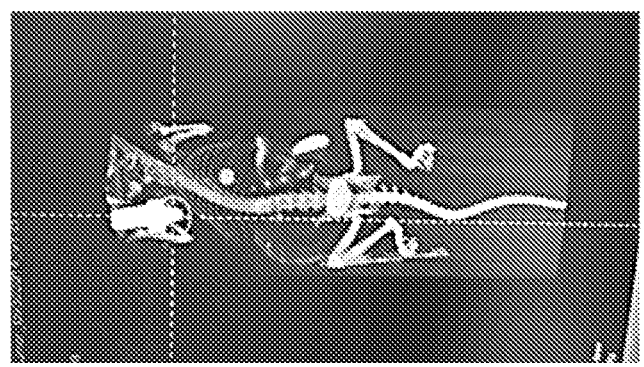
Figure 13:
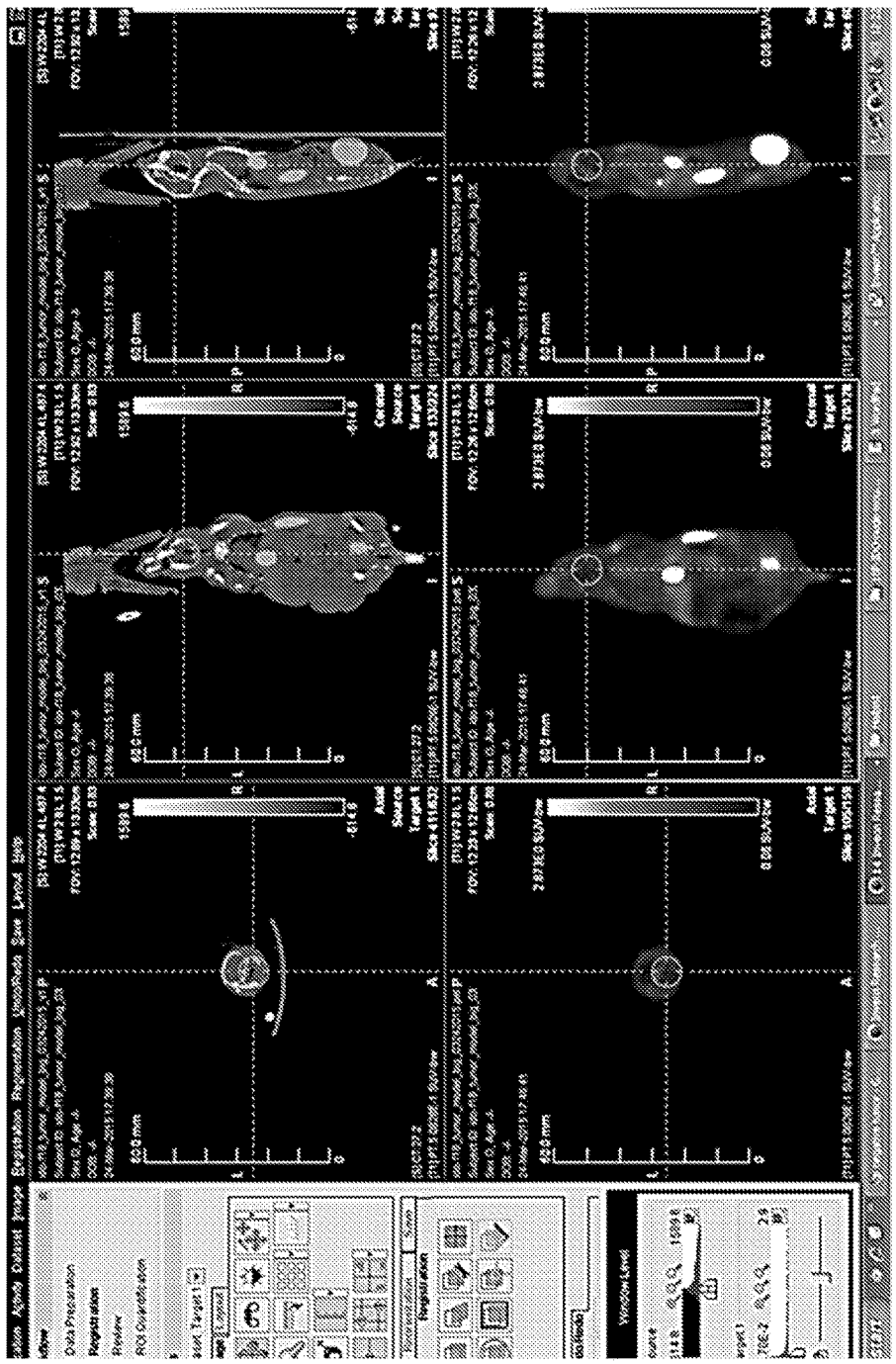
FIGS. 13-15. Decay-corrected whole-body $^{18}$F-IDO5L 3D microPET/CT imaging in a MDA-MB231 xenograft breast cancer mouse model from a dynamic scan at 10 minutes, 30 minutes, and 60 minutes after injection.
Figure 14:
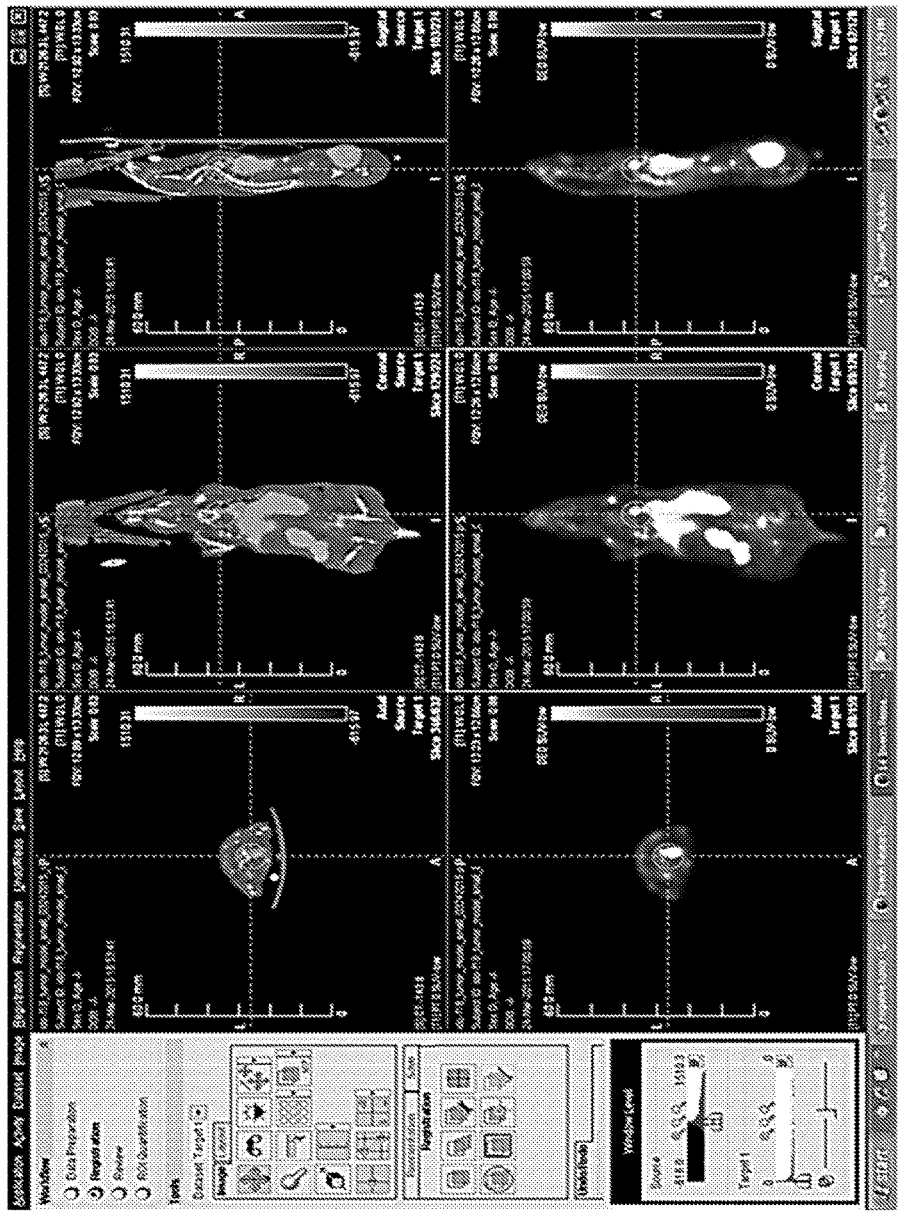
Figure 15:
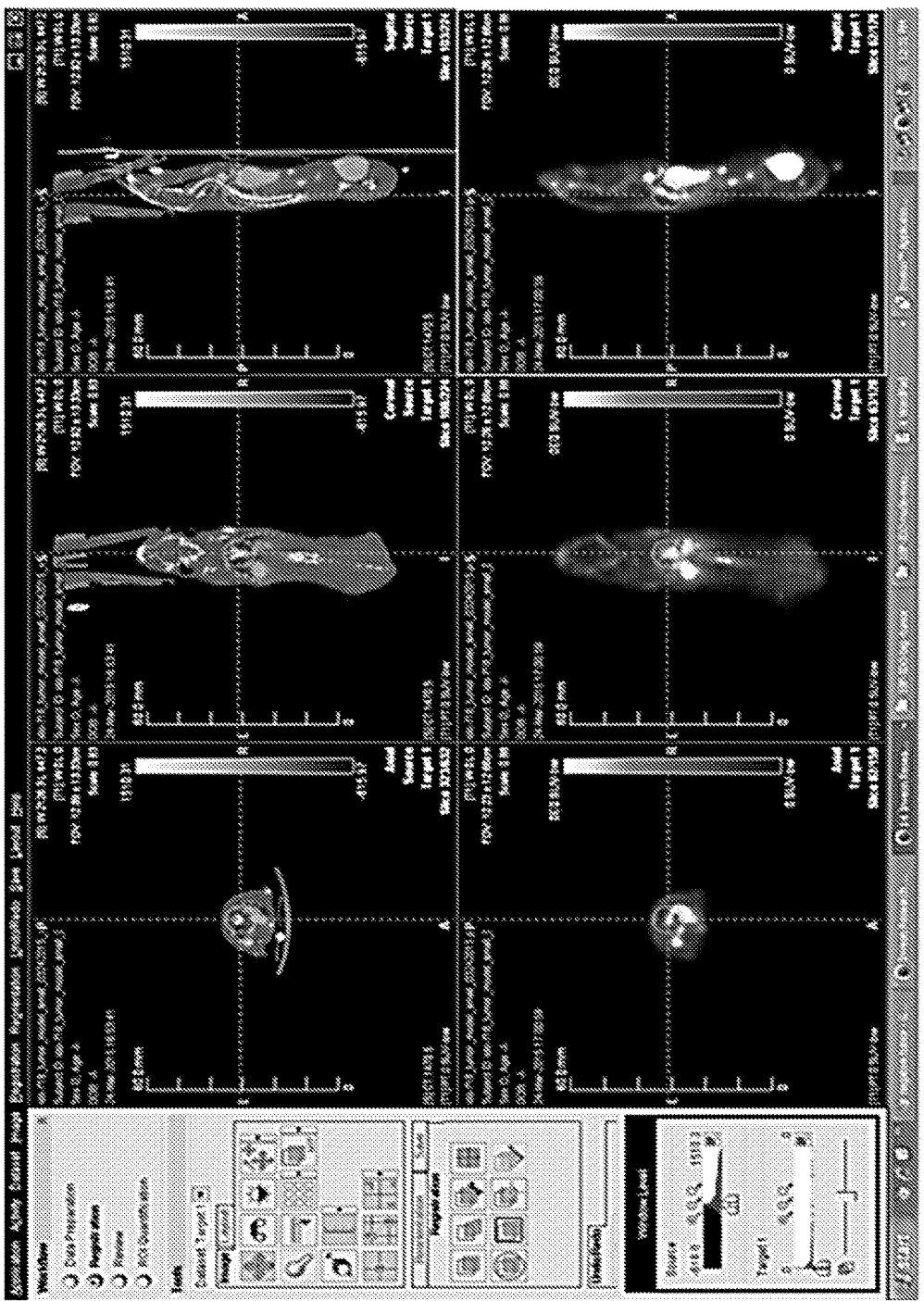

The final step is the coupling of compound 3 with 18F-12 to give [18F]IDO5L under base conditions. To neutralize remaining HCl and basicify the reaction mixture, excess amount of three different bases (100 μL Et3N, 300 μL 1M NaHCO3, and 150 μL 1M Na2CO3) was tested. Among them, NaHCO$_3$ gave the best labeling yield (51-64%) of [$^{18}$F]IDO5L determined by radio-TLC (FIG. 2C), while Et$_3$N produced no labeled product, and Na$_2$CO$_3$ gave low radiochemistry yield (<40%). Considering the absence of compound 3 and the presence of unreacted $^{18}$F-12 in HPLC profiles of the crude products, the inventors hypothesized that decomposition of compound 3 under base condition is a major side reaction. Therefore, lower labeling yield achieved under Na$_2$CO$_3$ can be explained as a stronger base caused faster decomposition of compound 3. After filtration, [$^{18}$F]IDO5L was purified by preparative HPLC and eluted at 10.9-11.7 min (FIG. 3). Formulation of the labeled product for i.v. injection was prepared as follows: The HPLC solvents were first diluted with water and then passed through C18 Sep-Pak column. After being washed with water, the [$^{18}$F]IDO5L was eluted by methanol. The elution solvent was removed by evaporation, and the residue was redissolved in physiological saline. The identity of the new tracer [$^{18}$F]IDO5L was confirmed in HPLC analysis by coinjection with IDO5L (FIG. 4). Typically, starting from 0.34 to 0.74 GBq (9.2-19.9 mCi) [$^{18}$F]fluoride, 35 to 77 MBq (0.94-2.09mCi) of purified [$^{18}$F]IDO5L could be obtained in ~90 min. The overall three-step decay-corrected radiochemical yield was 18.2+2.1% (n=4) with the radiochemical purity exceeding 98%. Specific activity, determined by using online measurements of radioactivity and UV absorption, was 11-15 GBq/μmol at end of synthesis.

In conclusion, the inventors explored [$^{18}$F]-labeled aniline as intermediate in [$^{18}$F]-radiolabeling chemistry for the facile radiosynthesis of 4-amino-N-(3-chloro-4-fluorophenyl)-N'-hydroxy-1,2,5-oxadiazole-3-carboximidamide [$^{18}$F]IDO5L as a novel IDO1-targeted tracer. The tracer has been synthesized and optimized by a three-step radiolabeling method with good radiochemical yield. PET imaging studies are currently being carried out in various cancer animal models to evaluate the in vivo potential of this IDO1 inhibitor.

All patents, patent applications, provisional applications, and publications referred to or cited herein are incorporated by reference in their entirety, including all figures and tables, to the extent they are not inconsistent with the explicit teachings of this specification.

Exemplified Embodiments

Examples of claimed embodiments of the invention include, but are not limited to:

1. An $^{18}$F labeled IDO1 imaging construct, comprising a molecule of the structure:

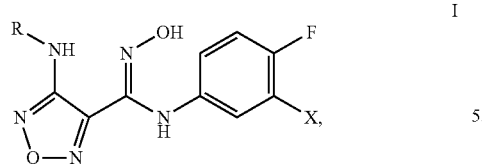

I wherein X is a halogen, and R is H, C$_1$-C$_8$ alkyl, C$_1$-C$_8$ alkylcarbonyl, phenyl, phenylcarbonyl, and wherein R is optionally substituted with one or more C$_1$-C$_8$ alkyl, phenyl, phenylHC=N—O—, wherein the substituent is optionally substituted with a fluorine, and wherein at least one fluorine of the structure is $^{18}$F.

2. The $^{18}$F labeled IDO1 imaging construct according to embodiment 1, wherein the molecule has the structure selected from:

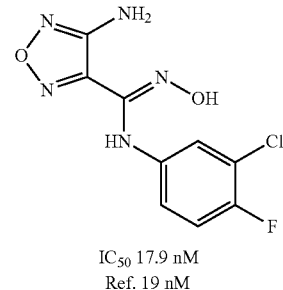

IDO-5l

IC$_{50}$ 17.9 nM
Ref. 19 nM

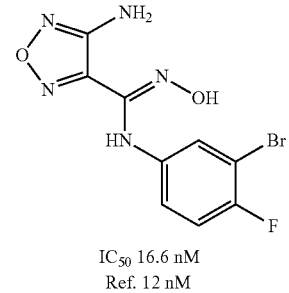

IDO-5m

IC$_{50}$ 16.6 nM
Ref. 12 nM

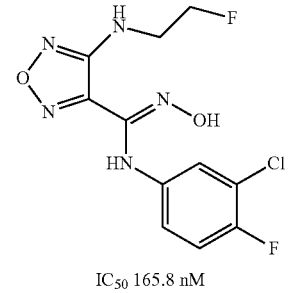

IDO 4-9

IC$_{50}$ 165.8 nM

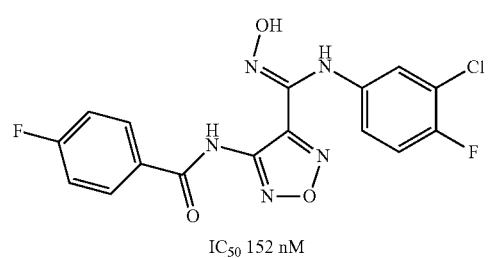

IDO 6

IC$_{50}$ 152 nM

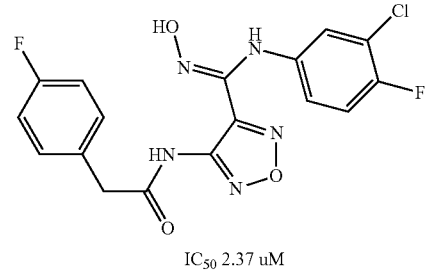

IDO 5

IC$_{50}$ 2.37 uM

-continued

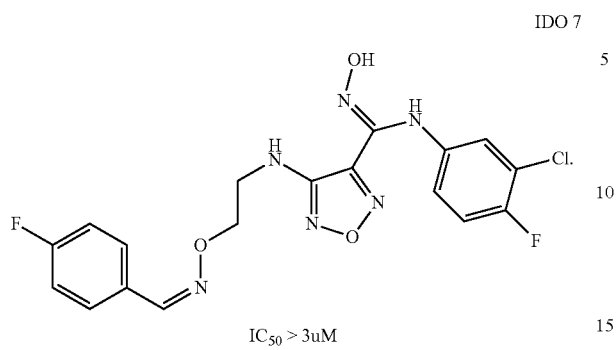

IDO 7

IC₅₀ > 3uM

3. A method of preparing an $^{18}F$ labeled IDO1 imaging construct according to embodiment 1 or 2, comprising:
providing 4-amino-N-hydroxy-1,2,5-oxadiazole-3-carboximidoyl chloride of the structure:

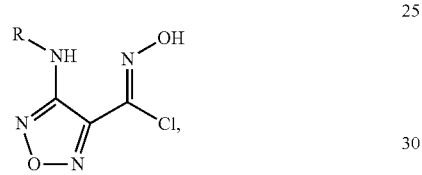

wherein R is H, $C_1$-$C_8$ alkyl, $C_1$-$C_8$ alkylcarbonyl, phenyl, phenylcarbonyl, wherein R is optionally substituted with one or more $C_1$-$C_8$ alkyl, phenyl, phenylHC=N—O—, wherein the substituent is optionally substituted with a fluorine;
providing a 4-amino-N-hydroxy-1,2,5-oxadiazole-3-carboximidoyl chloride; and
isolating an $^{18}F$ labeled IDO1 imaging construct according to embodiment 1, wherein the 1-fluoro-2-halo-4-aminobenzene and/or the 4-amino-N-hydroxy-1,2,5-oxadiazole-3-carboximidoyl chloride comprises an $^{18}F$.

4. The method according to embodiment 3, wherein providing a 4-amino-N-hydroxy-1,2,5-oxadiazole-3-carboximidoyl chloride comprises:
providing a 2-halo-N,N,N-trimethyl-4-nitrobenzenaminium trifluoromethanesulfonate;
combining the 2-halo-N,N,N-trimethyl-4-nitrobenzenaminium trifluoromethanesulfonate with cryptated potassium fluoride in an organic solvent to form a 1-fluoro-2-halo-4-nitrobenzene;
combining the 1-fluoro-2-halo-4-nitrobenzene with NaBH₄ and a Pd/C catalyst in an organic solvent to form the 1-fluoro-2-halo-4-aminobenzene.

5. A method of performing positron emission tomography (PET), comprising injecting a solution comprising an $^{18}F$ labeled IDO1 imaging construct according to embodiment 1 or 2 into a patient suspected of having cancer.

6. The method according to embodiment 5, wherein the molecule has the structure selected from:

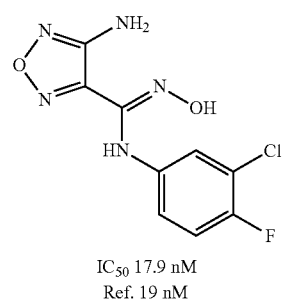

IDO-51

IC₅₀ 17.9 nM
Ref. 19 nM

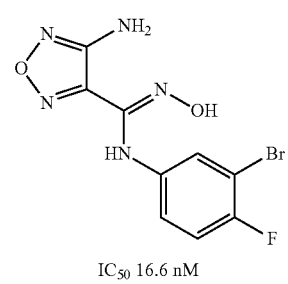

IDO-5m

IC₅₀ 16.6 nM
Ref. 12 nM

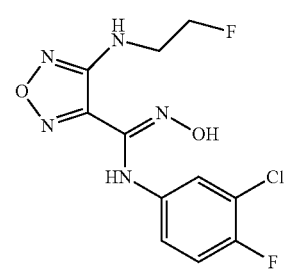

IDO 4-9

IC₅₀ 165.8 nM

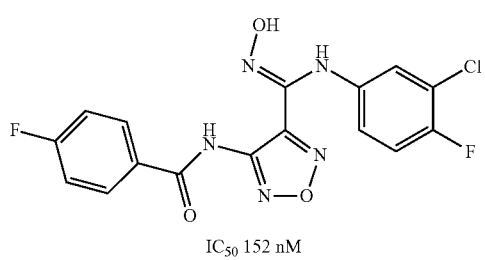

IDO 6

IC₅₀ 152 nM

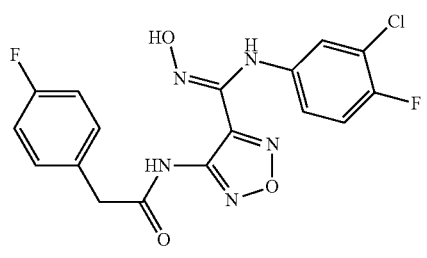

IDO 5

IC₅₀ 2.37 uM

-continued

IDO 7

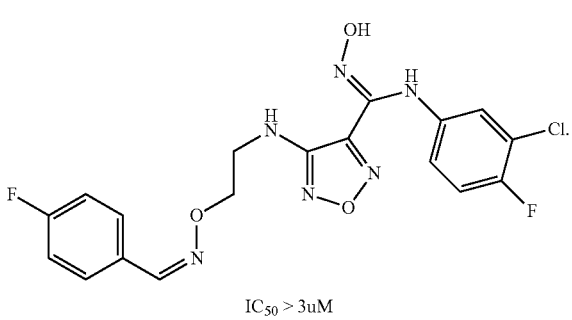

IC$_{50}$ > 3uM

7. The method according to embodiment 5, wherein the cancer is breast cancer.

8. The method according to any one of embodiments 5 to 7, further comprising administering a treatment for the cancer to the patient before, during, or after injecting the solution.

9. The method according to embodiment 8, wherein the treatment comprises administration of surgery, radiation, chemotherapy, immunotherapy, or a combination of two or more of the foregoing.

10. The method according to any one of embodiments 5 to 9, wherein the cancer is one in which indoleamine 2,3-dioxygenase-1 (IDO1) is over-expressed relative to normal tissue.

11. The method according to any one of embodiments 5 to 10, wherein the treatment comprises administering an inhibitor of indoleamine 2,3-dioxygenase-1 (IDO1) to the patient.

12. The method according to any one of embodiments 5 to 11, wherein the treatment comprises administering a combination of an inhibitor of indoleamine 2,3-dioxygenase-1 (IDO1) and a different cancer treatment simultaneously or consecutively.

13. The method according to embodiment 12, wherein the different treatment comprises radiation, chemotherapy, immunotherapy, or a combination of two or more of the foregoing.

14. The method according to any one of embodiments 5 to 13, wherein the patient is human.

15. The method according to any one of embodiments 5 to 13, wherein the patient is a non-human animal.

16. A method for treating cancer in a patient, comprising administering a treatment for the cancer to the patient; and injecting a solution comprising an $^{18}$F labeled IDO1 imaging construct according to embodiment 1 into the patient.

17. The method according to embodiment 16, wherein the treatment is administered before injecting the solution.

18. The method according to embodiment 16, wherein the treatment is administered after injecting the solution.

19. The method according to embodiment 16, wherein the solution is injected before administering the treatment to the patient, and the solution is administered after administering the treatment to the patient.

20. The method according to any one of embodiments 16 to 19, wherein the treatment comprises administration of surgery, radiation, chemotherapy, immunotherapy, or a combination of two or more of the foregoing.

21. The method according to any one of embodiments 16 to 20, wherein the cancer is one in which indoleamine 2,3-dioxygenase-1 (IDO1) is over-expressed relative to normal tissue.

22. The method according to any one of embodiments 16 to 21, wherein the treatment comprises administering an inhibitor of indoleamine 2,3-dioxygenase-1 (IDO1) to the patient.

23. The method according to any one of embodiments 16 to 22, wherein the treatment comprises administering a combination of an inhibitor of indoleamine 2,3-dioxygenase-1 (IDO1) and a different cancer treatment simultaneously or consecutively.

24. The method according to embodiment 23, wherein the different treatment comprises radiation, chemotherapy, immunotherapy, or a combination of two or more of the foregoing.

25. The method according to any one of embodiments 16 to 24, wherein the patient is human.

26. The method according to any one of embodiments 16 to 24, wherein the patient is a non-human animal.

REFERENCES

[1] X. Liu, R. C. Newton, S. M. Friedman, P. A. Scherle, Curr. Cancer Drug Targets 2009, 9, 938.

[2] C. X. Uyttenhove, L. Pilotte, I. Theate, V. Stroobant, D. Colau, N. Parmentier, T. Boon, B. J. Van den Eynde, Nat. Med. 2003, 9, 1269.

[3] D. H. Munn, E. Shafizadeh, J. T. Attwood, I. Bondarev, A. Pashine, A. L. Mellor, J. Expt. Med. 1999, 189, 1363.

[4] M. Friberg, R. Jennings, M. Alsarraj, S. Dessureault, A. Cantor, M. Extermann, A. L. Mellor, D. H. Munn, S. J. Antonia, Int. J. Cancer 2002, 101, 151.

[5] A. J. Muller, J. B. DuHadaway, P. S. Donover, E. Sutanto-Ward, G. C. Prendergast, Nat. Med. 2005, 11, 312.

[6] X. Liu, N. Shin, H. K. Koblish, G. Yang, Q. Wang, K. Wang, L. Leffet, M. J. Hansbury, B. Thomas, M. Rupar, P. Waeltz, K. J. Bowman, P. Polam, R. B. Sparks, E. W. Yue, Y. Li, R. Wynn, J. S. Fridman, T. C. Burn, A. P. Combs, R. C. Newton, P. A. Scherle, Blood 2010, 115, 3520.

[7] H. K. Koblish, M. J. Hansbury, K. J. Bowman, G. Yang, C. L. Neilan, P. J. Haley, T. C. Burn, P. Waeltz, R. B. Sparks, E. W. Yue, A. P. Combs, P. A. Scherle, K. Vaddi, J. S. Fridman, Mol. Cancer Ther. 2010, 9, 489.

[8] T. Yoshikawa, T. Hara, H. Tsurumi, N. Goto, M. Hoshi, J. Kitagawa, N. Kanemura, S. Kasahara, H. Ito, M. Takemura, K. Saito, M. Seishima, T. Takami, H. Moriwaki, Eur. J. Haematol. 2010, 84, 304.

[9] V. Lindstrom, J. Aittoniemi, J. Jylhivi, C. Eklund, M. Hurme, T. Paavonen, S. S. Oja, M. Itala-Remes, M. Sinisalo, Clin Lymphoma Myeloma Leuk 2012, 12, 363.

[10] X.-Q. Liu, K. Lu, L.-L. Feng, M. Ding, J.-M. Gao, X.-L. Ge, X. Wang, Leuk. Lymphoma 2013, 55, 405.

[11] The clinical trials website. https://www.clinicaltrials.gov/ct2/results?term=NCT01604889, https://www.clinicaltrials.gov/ct2/results?term=NCT01961115, https://www.clinicaltrials.gov/ct2/results?term=NCT01042535.

[12] C. Batista, C. Juhisz, O. Muzik, W. Kupsky, G. Barger, H. Chugani, S. Mittal, S. Sood, P. Chakraborty, D. Chugani, Mol. Imaging Biol. 2009, 11, 460.

[13] C. Juhisz, O. Muzik, X. Lu, M. S. Jahania, A. O. Soubani, M. Khalaf, F. Peng, T. J. Mangner, P. K. Chakraborty, D. C. Chugani, J. Nucl. Med. 2009, 50, 356.

[14] E. W. Yue, B. Douty, B. Wayland, M. Bower, X. Liu, L. Leffet, Q. Wang, K. J. Bowman, M. J. Hansbury, C. Liu, M. Wei, Y. Li, R. Wynn, T. C. Burn, H. K. Koblish, J. S. Fridman, B. Metcalf, P. A. Scherle, A. P. Combs, J. Med. Chem. 2009, 52, 7364.

[15] Y. Seimbille, M. E. Phelps, J. Czemin, D. H. S. Silverman, J. Label Compds. Radiopharm. 2005, 48, 829.
[16] H. F. Vanbrocklin, J. P. O'Neil, D. L. Hom, A. R. Gibbs, J. Label Compds. Radiopharm. 2001, 44, S880.

We claim:

1. An $^{18}$F labeled IDO1 imaging construct, comprising a molecule having the following structure:

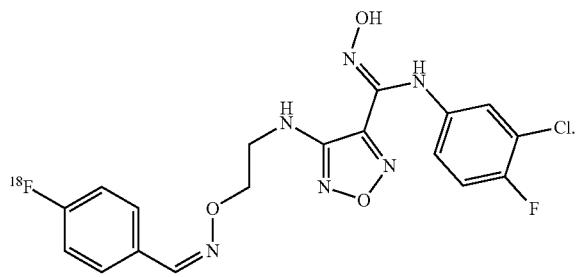 [SMILES: O/N=C(\Nc1ccc(F)c(Cl)c1)c1nonc1NCCO/N=C\c1ccc([18F])cc1]

2. A method of performing positron emission tomography (PET), comprising injecting a solution comprising an $^{18}$F labeled IDO1 imaging construct into a patient suspected of having cancer; and imaging the patient with PET, wherein the $^{18}$F labeled IDO1 imaging construct comprises a molecule having the following structure:

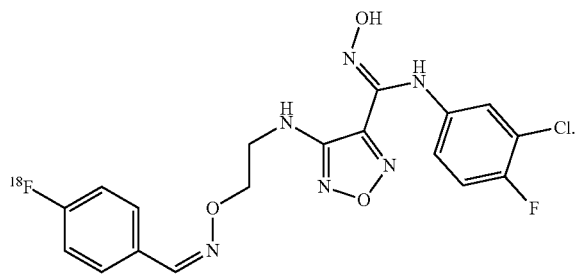 [SMILES: O/N=C(\Nc1ccc(F)c(Cl)c1)c1nonc1NCCO/N=C\c1ccc([18F])cc1]

3. The method according to claim 2, wherein the cancer is breast cancer.

4. The method according to claim 2, further comprising administering a treatment for the cancer to the patient before, during, or after injecting the solution.

5. The method according to claim 4, wherein the treatment comprises administration of surgery, radiation, chemotherapy, immunotherapy, or a combination of two or more of the foregoing.

6. The method according to claim 4, wherein the treatment comprises administering an inhibitor of indoleamine 2,3-dioxygenase-1 (IDO1) to the patient.

7. The method according to claim 4, wherein the treatment comprises administering a combination of an inhibitor of indoleamine 2,3-dioxygenase-1 (IDO1) and a different cancer treatment simultaneously or consecutively.

8. The method according to claim 4, wherein the patient is human.

9. A method for treating cancer in a patient, comprising administering a treatment for the cancer to the patient; and injecting a solution comprising an $^{18}$F labeled IDO1 imaging construct into the patient, wherein the $^{18}$F labeled IDO1 imaging construct comprises a molecule having the following structure:

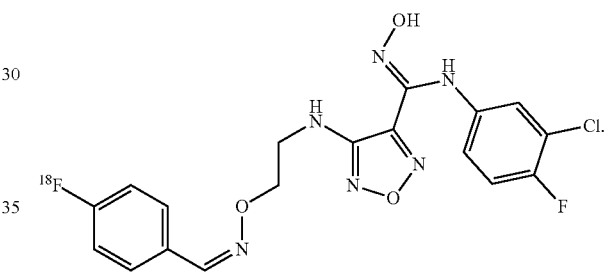

* * * * *